US011318025B2

(12) United States Patent
Schipper et al.

(10) Patent No.: US 11,318,025 B2
(45) Date of Patent: May 3, 2022

(54) SYSTEM AND METHOD FOR PREOPERATIVE PLANNING FOR TOTAL HIP ARTHROPLASTY

(71) Applicant: INTELLIJOINT SURGICAL INC., Kitchener (CA)

(72) Inventors: Joseph Arthur Schipper, Kitchener (CA); Andre Novomir Hladio, Waterloo (CA); Samantha Lynn McCabe, Kitchener (CA); Jonathan Matthew Vigdorchik, Brooklyn, NY (US)

(73) Assignee: INTELLIJOINT SURGICAL INC., Kitchener (CA)

( * ) Notice: Subject to any disclaimer, the term of this patent is extended or adjusted under 35 U.S.C. 154(b) by 213 days.

(21) Appl. No.: 16/754,020

(22) PCT Filed: Oct. 4, 2018

(86) PCT No.: PCT/CA2018/051253
§ 371 (c)(1),
(2) Date: Apr. 6, 2020

(87) PCT Pub. No.: WO2019/068194
PCT Pub. Date: Apr. 11, 2019

(65) Prior Publication Data
US 2020/0323649 A1 Oct. 15, 2020

Related U.S. Application Data

(60) Provisional application No. 62/691,912, filed on Jun. 29, 2018, provisional application No. 62/569,106, filed on Oct. 6, 2017.

(51) Int. Cl.
*A61F 2/46* (2006.01)
*G16H 20/40* (2018.01)
(Continued)

(52) U.S. Cl.
CPC .............. *A61F 2/46* (2013.01); *A61F 2/34* (2013.01); *A61F 2/36* (2013.01); *G06T 17/00* (2013.01);
(Continued)

(58) Field of Classification Search
CPC combination set(s) only.
See application file for complete search history.

(56) References Cited

U.S. PATENT DOCUMENTS 9,665,686 B2 * 5/2017 Van Vorhis ............ G16H 20/40
10,705,677 B2 * 7/2020 Andersson .......... G06F 3/04815
(Continued)

FOREIGN PATENT DOCUMENTS

| EP | 1173105 A1 | 1/2002 |
| WO | 2006091494 A1 | 8/2006 |

(Continued)

OTHER PUBLICATIONS

Zheng, Guoyan, et al. "A hybrid CT-free navigation system for total hip arthroplasty." Computer Aided Surgery 7.3 (2002): 129-145.*
(Continued)

*Primary Examiner* — Ryan M Gray

(57) ABSTRACT

Planning tools for surgery, particularly for THA, are provided. Images of musculoskeletal structure of a patient (e.g. associated with respective planes and in a same or different functional position) may be displayed together and via co-registration and spatial transformations, 3D implants or other objects may be rendered and overlaid in a same position correctly with respect to each image. The 3D implant may be fit (e.g. via handles or automatically using image processing) to an existing implant in the patient and moved to other positions, for example, to measure the existing position or plan for an initial or new position. Measures may be represented with respect to various planes
(Continued)

associated with the respective image and/or with respect to an existing implant.

22 Claims, 28 Drawing Sheets

(51) Int. Cl.
    *G16H 30/40*     (2018.01)
    *A61F 2/34*     (2006.01)
    *A61F 2/36*     (2006.01)
    *G06T 17/00*     (2006.01)
    *G06T 19/00*     (2011.01)
    *G06T 19/20*     (2011.01)

(52) U.S. Cl.
    CPC ............ *G06T 19/006* (2013.01); *G06T 19/20* (2013.01); *G16H 20/40* (2018.01); *G16H 30/40* (2018.01); *A61F 2002/4633* (2013.01); *G06T 2200/24* (2013.01); *G06T 2219/2004* (2013.01)

(56) References Cited

U.S. PATENT DOCUMENTS

| | | | | |
|---|---|---|---|---|
| 2015/0088146 A1* | 3/2015 | McCarthy | .......... | A61B 17/1666 606/91 |
| 2015/0238272 A1* | 8/2015 | Ranawat | ............ | A61B 17/1746 703/11 |
| 2016/0100909 A1* | 4/2016 | Wollowick | ................ | G06T 7/33 600/424 |
| 2017/0340389 A1* | 11/2017 | Otto | ........................ | A61B 34/10 |
| 2018/0161101 A1* | 6/2018 | Barsoum | .................. | A61F 2/32 |
| 2020/0281728 A1* | 9/2020 | Kulper | .................. | G16H 30/40 |
| 2021/0183075 A1* | 6/2021 | Schipper | ................ | G06T 7/246 |

FOREIGN PATENT DOCUMENTS

| | | |
|---|---|---|
| WO | 2011160008 A1 | 12/2011 |
| WO | 2012100825 A1 | 8/2012 |

OTHER PUBLICATIONS

International Search Report dated Jan. 18, 2019; 6 Pages for Corresponding International PCT Patent Application No. PCT/CA2018/051253.
Written Opinion dated Jan. 18, 2019; 6 Pages for Corresponding International PCT Patent Application No. PCT/CA2018/051253.
Loppini et al., The Journal of Arthroplasty, 2017, 6 Pages.
Tannast et al., Estimation of Pelvic Tilt on Anteroposterior X-Rays—A Comparison of Six Parameters, 2006, 7 Pages.
Extended European Search Report Issued by the European Patent Office for Corresponding European Patent Application No. 18863932.2, dated Jun. 4, 2021, 13 Pages.

* cited by examiner

1100

```
┌─────────────────────────────────────────────────────────────────────┐
│ Access and display at least three images of a musculoskeletal       │
│ structure of a patient, where one pair of images are of different   │
│ views of a first position, and another pair of images are of the    │
│ same view in different functional positions        1102             │
└─────────────────────────────────────────────────────────────────────┘
                                  ↓
┌─────────────────────────────────────────────────────────────────────┐
│ Define reference axes of the musculoskeletal structure on at least  │
│ two images, based on user input                    1104             │
└─────────────────────────────────────────────────────────────────────┘
                                  ↓
┌─────────────────────────────────────────────────────────────────────┐
│ Determine a positional change parameter of the musculoskeletal      │
│ structure based on the two images of a common view in different     │
│ functional positions, the positional change parameter representing  │
│ the positional change of the patient between the functional         │
│ positions                                          1106             │
└─────────────────────────────────────────────────────────────────────┘
                                  ↓
┌─────────────────────────────────────────────────────────────────────┐
│ Determine spatial transformations between the images    1108        │
└─────────────────────────────────────────────────────────────────────┘
                                  ↓
┌─────────────────────────────────────────────────────────────────────┐
│ Render and overlay a 3D implant for each image in a first position  │
│ relative to the reference axes, and according to the respective     │
│ spatial transformations, on the respective images       1110        │
└─────────────────────────────────────────────────────────────────────┘
                                  ↓
┌─────────────────────────────────────────────────────────────────────┐
│ Receive input representing a second position            1112        │
└─────────────────────────────────────────────────────────────────────┘
                                  ↓
┌─────────────────────────────────────────────────────────────────────┐
│ Update, in at least near real time, the render and overlay          │
│ accordingly for each image                              1114        │
└─────────────────────────────────────────────────────────────────────┘
```

Fig. 11

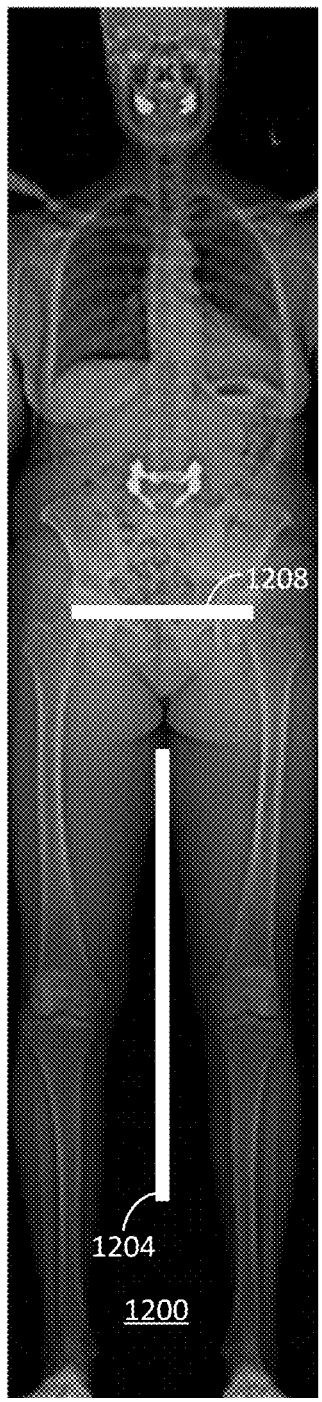
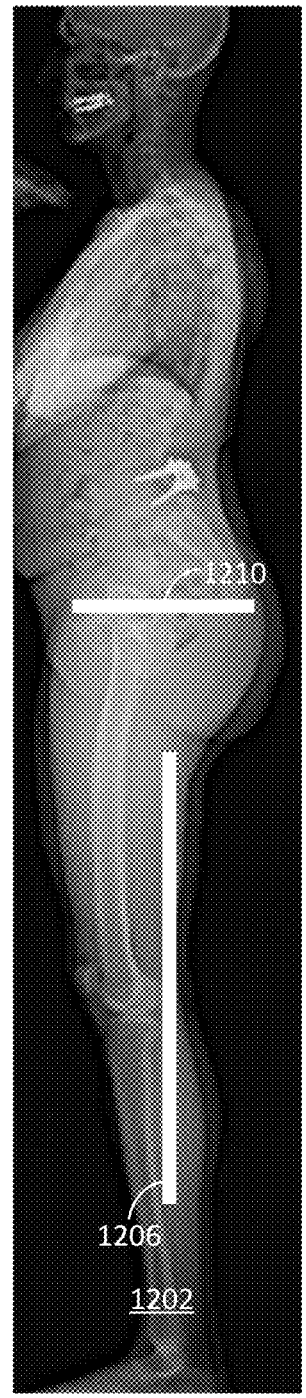
Fig. 12A
Fig. 12B

2800

Access and display at least two images of a musculoskeletal structure of a patient, where one pair of images are of different views of a first position or are of a same view in different functional positions  2802

Define reference axes of the musculoskeletal structure on at least one of the at least two images, based on user input  2804

Determine a spatial transformation between the at least two images based on the reference axes  2806

Determine a positional change parameter of the musculoskeletal structure if one pair of the at least two images is the same view in different functional positions, the positional change parameter representing the positional change of the patient between the different functional positions  2808

Render and overlay a 3D implant respectively for each of the images in a first position relative to the reference axes and according to the spatial transformation and the positional change parameter, if applicable  2810

Render and overlay respectively for each of the three images a safe zone graphical element indicating a clinically accepted safe range of positions for the 3D implant 2812

Fig. 28

SYSTEM AND METHOD FOR PREOPERATIVE PLANNING FOR TOTAL HIP ARTHROPLASTY

CROSS-REFERENCE

This application claims, in respect of the United States, the domestic benefit of, and in respect of other jurisdictions, Paris convention priority to the following applications: 1) U.S. Provisional Application No. 62/569,106 filed Oct. 6, 2017 and entitled "System and Method for Preoperative Planning for Total Hip Arthroplasty" and 2) U.S. Provisional Application No. 62/691,912 filed Jun. 29, 2018 and entitled "System and Method for Preoperative Planning for Total Hip Arthroplasty", the entire contents of each application are incorporated herein by reference in respect of any jurisdiction where incorporation is permitted.

FIELD

The subject matter relates to computer assisted procedures in surgery including methods and systems therefor and more particularly to a system and method for preoperative planning such as for total hip arthroplasty.

BACKGROUND

This specification and the associated drawings will use hip replacement surgery as the primary example; this example is intended on being non-limiting, and the systems and methods described herein may be applied to various other surgical procedures or musculoskeletal diagnoses.

Hip replacement surgery (or Total Hip Arthroplasty, THA) involves replacing a patient's native hip (proximal femur and acetabulum) with prosthetic implants. The position of the implants is important for the function of the new joint. For example, a misaligned acetabular cup may dislocate post-operatively, and a malpositioned femur stem may cause periprosthetic fracture or leg length inequality. When referring to an implanted prosthesis, the term "position" may refer to clinically relevant parameters such as translational position relative to a bone or angular position relative to anatomical axes; the term "position" is intended to be interpreted based on the context of its use by one skilled in the art. In a hip replacement surgery, the position of individual implants is important, as is the combined position of both sides of the prosthetic joint (for example, the combined anteversion of a hip joint is the sum of the acetabular and femoral anteversion angles, and is known to be clinically relevant for hip joint stability).

The ideal position of joint implants may be patient specific, and in particular, dependent on a patient's functional musculoskeletal kinematics (i.e. how the various musculoskeletal structures move through functional positions). A functional position or movement generally means the biomechanics and kinematics of a musculoskeletal system during basic, everyday tasks (particularly those tasks essential to maintaining a basic quality of life, such as standing up, sitting down, mounting stairs, etc.). For example, in a healthy musculoskeletal system, the pelvis tilts in the sagittal plane between a standing and sitting position. Patients with abnormal musculoskeletal systems (e.g. hypermobile spine, degenerative disease and/or fused lumbar spines) may experience abnormal functional musculoskeletal kinematics, such as an abnormal degree of tilting in the sagittal plane from standing to sitting. For example, a stiff spine may cause the pelvis to have a relatively low change in tilt (posteriorly) when sitting, which results in abnormally high hip flexion, putting the patient at risk of impingement and/or dislocation. FIGS. 1A and 1B illustrate normal pelvic movement from the standing to the sitting position and FIGS. 2A and 2B illustrate abnormal pelvic movement from the standing to the sitting position, where the abnormality is the result of spinal stiffness, as illustrated by the spinal hardware. In addition to affecting the change in tilt between functional positions, deformity may also cause the musculoskeletal system position to deviate form a nominal healthy position (e.g. an unhealthy patient may have a pelvis tilted in the sagittal and/or coronal planes when standing normally).

SUMMARY

Disclosed are methods and systems to provided planning tools for surgery, particularly for THA. Images of musculoskeletal structure of a patient (e.g. associated with respective planes and in a same or different functional position) may be displayed together and via co-registration and spatial transformations, 3D implants or other objects may be rendered and overlaid in a same position correctly with respect to each image. The 3D implant may be fit (e.g. via handles or automatically using image processing) to an existing implant in the patient and moved to other positions, for example, to measure the existing position or plan for an initial or new position. Measures may be represented with respect to various planes associated with the respective image and/or with respect to an existing implant.

There is provided a computer implemented method comprising: accessing and displaying a standing AP image, a standing lateral image, and a sitting lateral image of a musculoskeletal structure of a patient; receiving respective axes coordinates on the standing AP image and standing lateral image respectively as input, and defining reference axes of the musculoskeletal structure on the standing AP image and the standing lateral image based on the respective axes coordinates; receiving respective tilt coordinates on the standing lateral image and the sitting lateral image respectively as input, and determining a change in tilt parameter between the standing AP image and the standing lateral image of the musculoskeletal structure based on the respective tilt coordinates; determining a spatial transformation between the standing AP image and the standing lateral image and a spatial transformation between the standing lateral image and the sitting lateral image; rendering and overlaying a 3D implant for each of the standing AP image and the standing lateral image in a first position relative to the reference axes based on the reference axes and the spatial transformation between the standing AP image and the standing lateral image; rendering and overlaying the 3D implant in the first position for the sitting lateral image based on the change in tilt parameter and the spatial transformation between the standing lateral image and the sitting lateral image; receiving input representing a second position of the 3D implant; and rendering and overlaying the 3D implant in the second position using each space transformation and the change in tilt parameter to update, in real time, each of the standing AP image, the standing lateral image and the sitting lateral image.

In the computer implemented method of claim 1 the images may be of any of the following modalities: x-ray, CT, MRI, EOS.

The computer implemented method may further comprise displaying change in tilt parameter.

In the computer implemented method, determining spatial transformations may comprise one or more of: performing computations based at least in part on the received coordinates; performing computations based on corresponding common features between received images; and performing computations based on known image acquisition spatial information.

In the computer implemented method the musculoskeletal structure may comprise a pelvis and the method may comprise planning for a total hip arthroplasty (THA) procedure.

In the computer implemented method the musculoskeletal structure may be a pelvis, the 3D implant may be an acetabular cup and the first position may be 40 degrees of inclination and 15 degrees of anteversion.

In the computer implemented method the first position may be based, at least in part, on the change in tilt parameter, and may be selected to maximize stability through functional patient movements.

The computer implemented method may further comprise: receiving templating information comprising one or more of implant size and desired location; and rendering the 3D implant according to at least a subset of the received templating information.

The computer implemented method may further comprise displaying a position information representing a current position of the 3D implant. In the computer implemented method the 3D implant may be an acetabular cup and the position information may be an inclination angle and an anteversion angle.

In the computer implemented method, the input representing the second position may be based on one or more of: a manipulation of an image associated with the 3D implant as overlaid on a one of the standing AP images, standing lateral image and sitting lateral image; and an inputting of numerical values. In the computer implemented method the manipulation of the image may comprise clicking and dragging a handle associated with the 3D implant overlay.

In the computer implemented method the images associated with the 3D implant and associated renderings may be provided for simultaneous display.

There is provided a computer implemented method comprising: accessing and displaying at least three images of a musculoskeletal structure of a patient, where one pair of images are of different views of a first position, and another pair of images are of the same view in different functional positions; defining reference axes of the musculoskeletal structure on at least two images, based on user input; determining a positional change parameter of the musculoskeletal structure based on the two images of a common view in different functional positions, the positional change parameter representing the positional change of the patient between the functional positions; determining spatial transformations between the images; rendering and overlaying a 3D implant for each image in a first position relative to the reference axes, and according to the respective spatial transformations, and overlaying the 3D implant renderings on the respective images; receiving input representing a second position; and updating, in at least near real time, the rendering and overlay accordingly for each image.

Complimentary computing device and computer program product aspects as well as other aspects and features will be apparent to one of ordinary skill in the art.

BRIEF DESCRIPTION OF THE DRAWINGS

FIGS. 10 and 11 are flowchart of respective operations of a computing device in accordance with the teachings herein.

FIGS. 12A and 12B are images of an anatomy from two views showing reference axes in each view.

FIG. 28 is a flowchart of operations of a computing device in accordance with the teachings herein.

DESCRIPTION

Figure 1A:
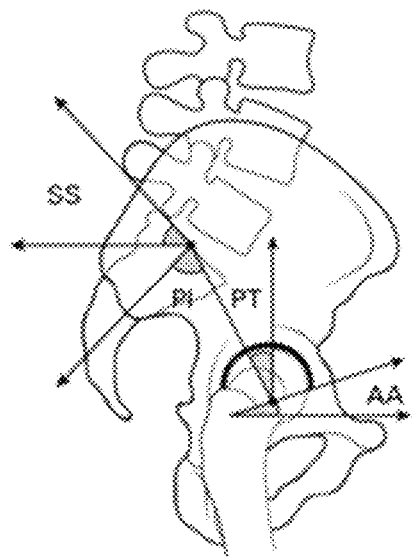
FIGS. 1A and 1B illustrate normal pelvic movement from the standing to the sitting position in accordance with the prior art.
Figure 1B:
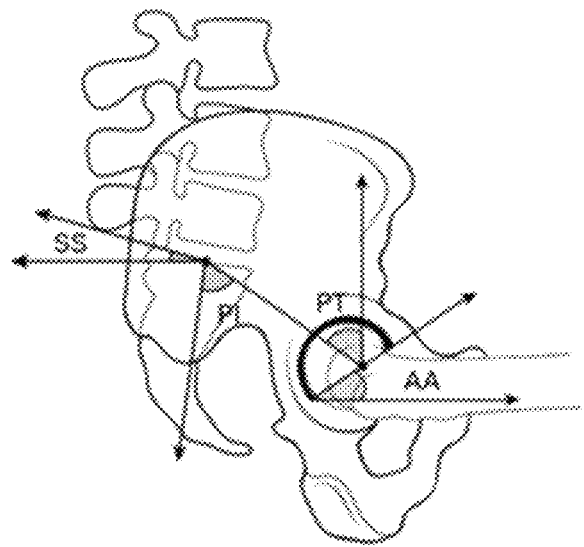

A computer-implemented method may help surgeons or other users to plan surgery with the goal of determining a desired or ideal implant position, based on functional musculoskeletal kinematics. The computer-implemented method may access a plurality of functional medical images, define reference axes in the images, determine the spatial transformations between the plurality of images, render a 3D model of an implant for each image according to the spatial transformations, and display the images along with an overlay based on the rendered 3D model corresponding to each image.

The functional medical images may include at least two images of different views of the patient's musculoskeletal region of interest. For example, an anterior-posterior (AP) view (i.e. the image plane corresponds to the patient's coronal plane), and a lateral view (i.e. the image plane corresponds with the patient's sagittal plane). The functional medical images may include at least two images in which the patient's musculoskeletal region of interest is in two different functional positions (e.g. standing and sitting).

The functional medical images may be of any modality where musculoskeletal structures can be visualized. For example, x-rays, computed tomography (CT) scans, magnetic resonance imaging (MRI) scans, EOS scans (EOS Imaging, Paris, France), etc. The medical images may be in DICOM, or any other digital format. All images may be of a single modality; alternatively, some images may be of differing modalities.

The functional medical images are related by spatial transformations. A spatial transformation between two images is the relative change in pose of the image reference frames with respect to the musculoskeletal region of interest. For example, the image reference frame of a pure AP view of a structure, and the image reference frame of a pure lateral view of the same structure mean the spatial transformation between the respective images is a rotation of 90° about the patient's longitudinal axis. The method of image acquisition, including the imaging modality, imaging equipment and imaging protocol, influences the spatial transformations. For example, some imaging equipment offers simultaneous perpendicular imaging capabilities. In this case the spatial transformation may be determined based on the imaging equipment. Parallax or other types of distortion may be inherent in certain imaging modalities; the respective spatial transformations may take into account the effects of such distortions.

In THA, the functional musculoskeletal kinematics of a patient may influence the ideal alignment of the acetabular cup implant. In particular, sagittal pelvic movement (or lack thereof) between functional positions may influence how the acetabular cup should be oriented to minimize risk of impingement and/or dislocation. The change in pelvic position in the sagittal plane may be measured by determining the pelvic orientation difference between two lateral x-ray images in different functional positions (e.g. standing and sitting). The change in pelvic position in the sagittal plane is also referred to as the change in pelvic tilt. Standing lateral x-rays of the musculoskeletal region of interest (i.e. the pelvis and proximal femur) may be performed in THA as part of routine diagnosis and planning; other functional images of the pelvis may also be obtained through defined x-ray protocols carried out by radiology staff. In such a protocol, the patient may be required to be accurately aligned with the x-ray cassette, and the affected hip to be close to and centered with respect to the cassette. X-ray parameters, such as the fixed focal distance, may be recorded or annotated in the resulting digital medical image (e.g. Digital Imaging and Communications in Medicine (DICOM®) format—DICOM is a registered trademark in the United States of the National Electrical Manufacturers Association). Standard format x-rays may be used to image the entire musculoskeletal region of interest, including the pelvis and proximal femur (and lumbar spine, if desired).

In THA, an AP Pelvis view is standard for pre-operative planning and templating, as well as for post-operative confirmation of implant position. An AP Pelvis and two functional images of a patient (pre- or post THA) may be accessed, for example, using a computer implemented method. The functional images may be a standing lateral and sitting lateral view of the patient's pelvic region. The images are provided for display. The AP Pelvis may be a standing AP pelvis.

Spatial transformations between each image may be partly set at the time of image acquisition. For example, in each x-ray, the cassette may be aligned with the direction of gravity (i.e. the y-axis of the resulting medical image is parallel to the direction of gravity). Partly setting the spatial transformations during image acquisition may decrease the number of steps required to determine the full spatial transformation.

Figure 3:
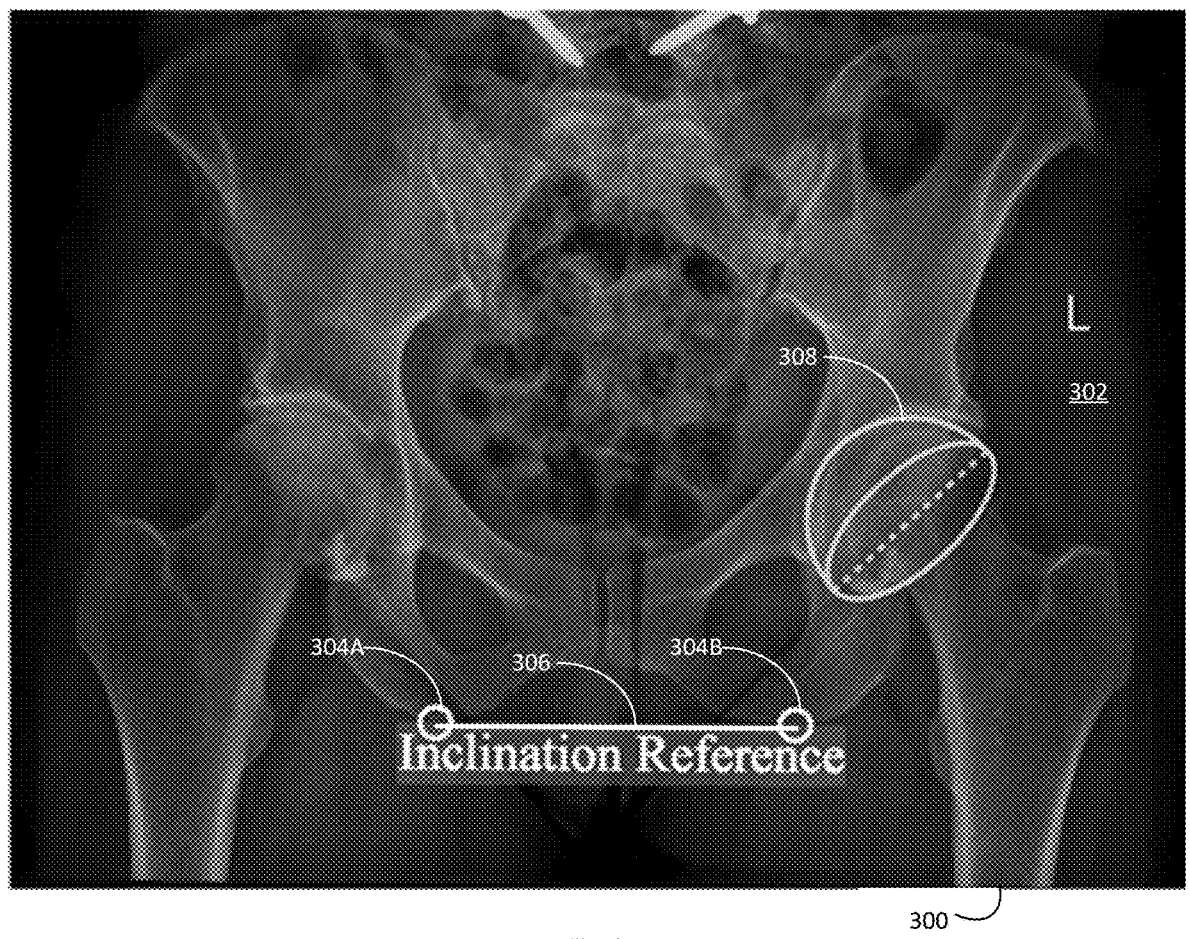
FIGS. 3-6 each illustrates a portion of a graphical user interface (GUI) configured to display images of an anatomy (e.g. the same anatomy from different views or in different positions) and enabled to receive input to define coordinates from positions on the screen that are associated to positions on the anatomy shown in the images.

With reference to FIG. 3, there is illustrated a portion of a graphical user interface (GUI) 300 configured to receive input to define coordinates from positions on the screen that are associated to positions on an anatomy shown in an x-ray. Coordinates on a standing AP x-ray 302 may be identified to set at least one reference axis. In FIG. 3, coordinates of the most inferior aspect of the bilateral ischial tuberosities may be identified by a user and received by a computer (e.g. a user clicking on both points 304A and 304B using a mouse or touch screen). In this case the reference axis 306 is denoted the "inclination reference" (though such need not be labelled on any GUI), since radiographic cup inclination may be measured relative to this axis. Other landmarks may be used to define this or any other reference axis, where the reference axis is a relevant axis to describe the position of the implant 308.

Figure 4:
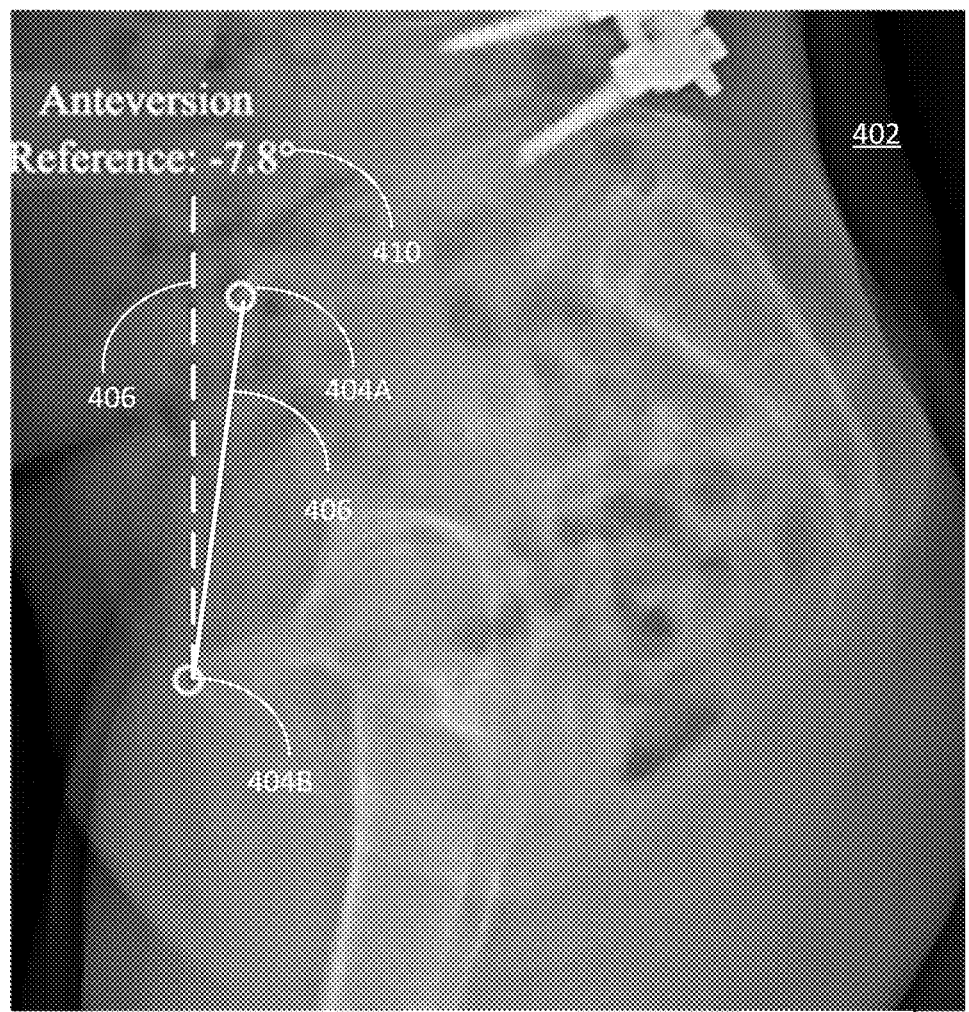

Coordinates on the standing lateral x-ray may be identified to set at least one reference axis. With reference to FIG. 4, there is illustrated a portion of a graphical user interface (GUI) 400 configured to receive input to define coordinates from positions on the screen that are associated to positions on an anatomy shown in an x-ray 402 (a standing lateral x-ray). In FIG. 4, coordinates of the Anterior Pelvic Plane (APP) (i.e., the anterior superior iliac spine (ASIS) and pubic symphysis) may be identified by a user and received by a computer (e.g. a user clicking on both points 404A and 404B using a mouse or touch screen). Optionally, the angle 410 between the reference axis 406 and the y-axis 408 (shown as a broken line) of the medical image may be computed and displayed. In this case the reference axis is denoted the "anteversion reference", since cup anteversion is zero when the cup face is perpendicular to this axis. The APP is a commonly used anatomical plane, representing the plane of the pelvis. Other landmarks may be used to define this or any other reference axis, where the reference axis is a relevant axis to describe the position of the implant.

Figure 5:
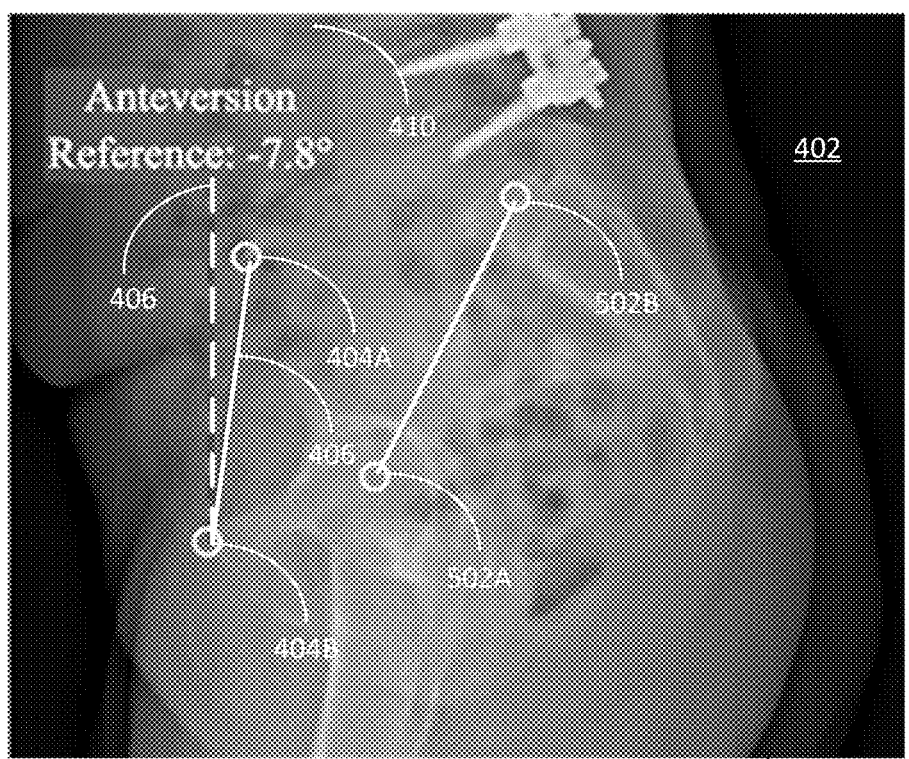

Coordinates on the standing lateral x-ray associated with the musculoskeletal structure (i.e. the pelvis) may be identified to establish a standing pelvic baseline position. With reference to FIG. 5, there is illustrated a portion of a graphical user interface (GUI) 400 as shown in FIG. 4 configured to receive input to define coordinates from positions on the screen that are associated to positions on an anatomy shown in an x-ray 402 (a standing lateral x-ray as in FIG. 4). In FIG. 5 the x-ray is enlarged (zoomed in). In FIG. 5, the center of the femoral head 502A and the midpoint of the sacral endplate 502B establish a standing pelvic baseline position. Coordinates on the sitting lateral x-ray corresponding to the same landmarks of the standing lateral x-ray are identified to determine a sitting pelvic position.

Figure 6:
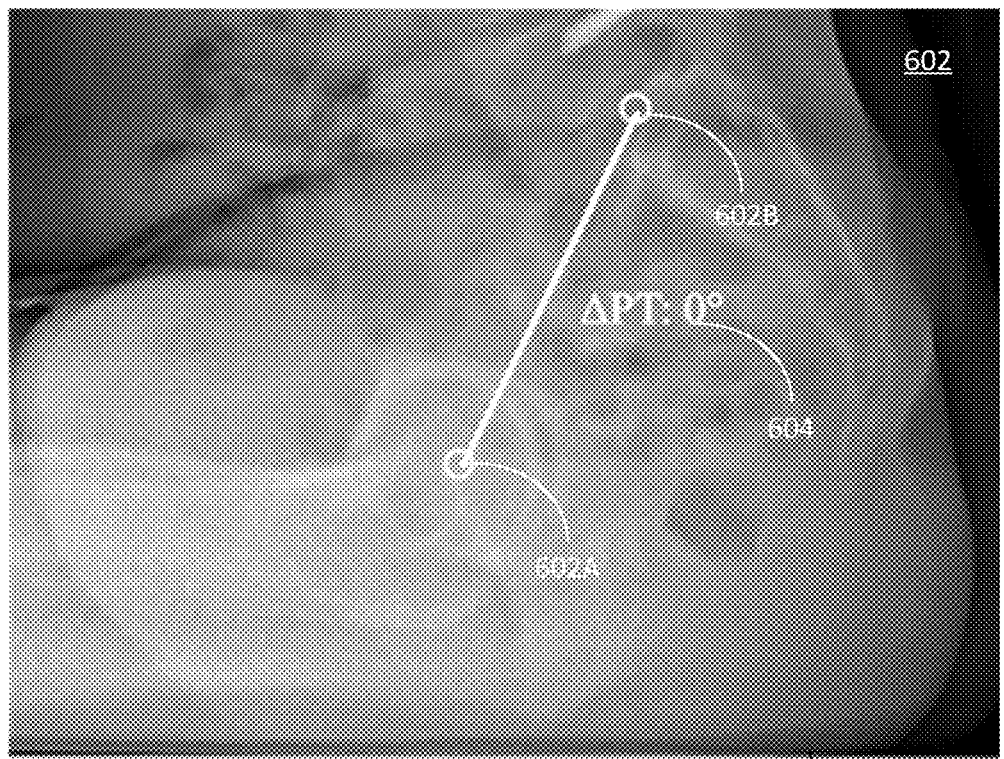

With reference to FIG. 6, there is illustrated a portion of a graphical user interface (GUI) 600 configured to receive input to define coordinates from positions on the screen that are associated to positions on an anatomy shown in an x-ray 602 (a sitting lateral x-ray). In FIG. 6, the center of the femoral head 602A and the midpoint of the sacral endplate 602B are again identified. A computing unit calculates the change in pelvic tilt angle based on the coordinates of the standing and lateral images. This angle may be displayed, as in FIG. 6 (ΔPT 604).

A GUI may be provided such as via a display device that provides a simultaneous display of two or more x-rays of a same anatomy such as from different views. The GUI may be configured to receive input to define coordinates for (e.g. over) each of the x-rays.

Figure 7:
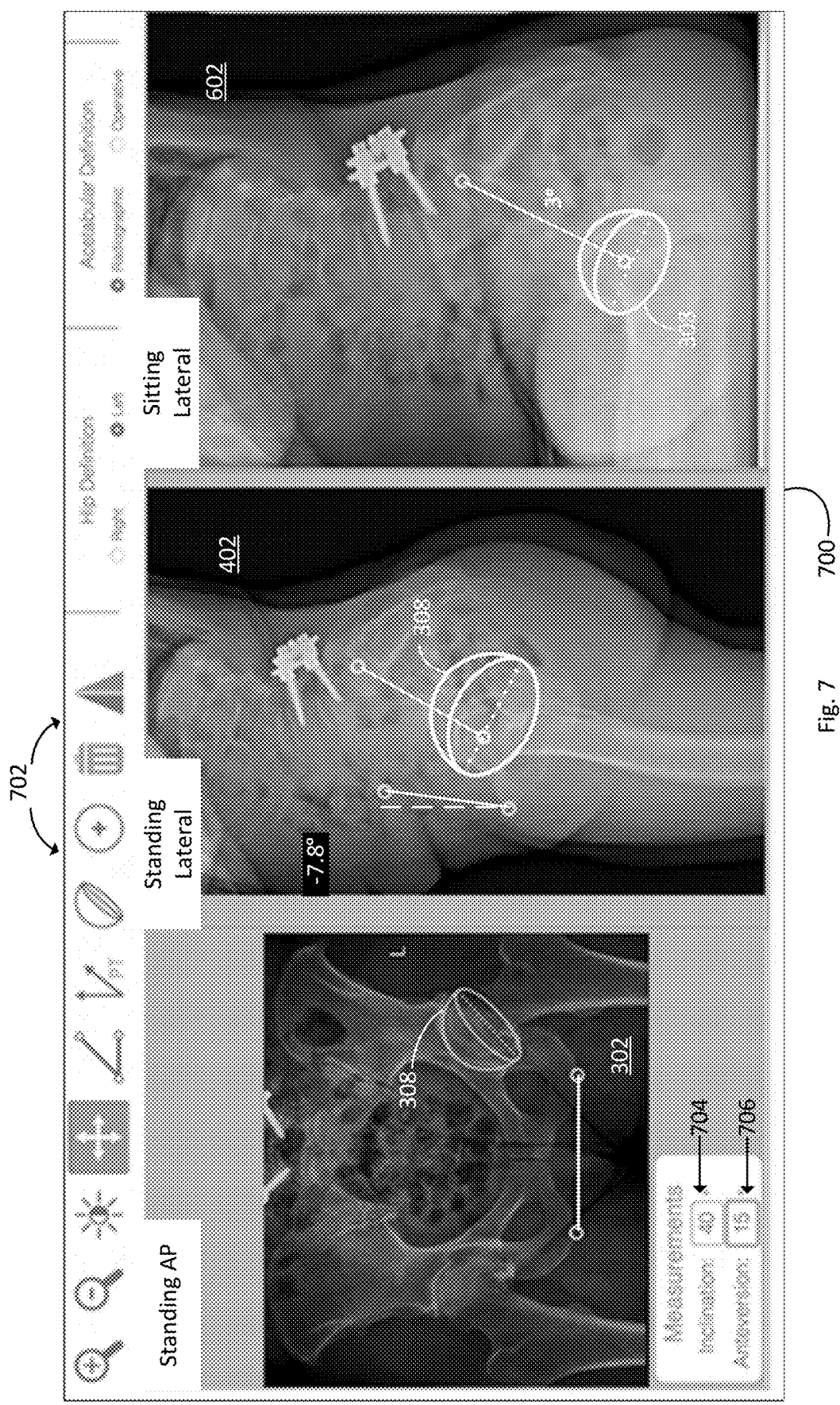
FIGS. 7 and 8 illustrate a GUI showing multiple images (e.g. x-rays) of a same anatomy simultaneously where the GUI is configured to receive input to define coordinates from positions on the screen that are associated to positions on the anatomy, among other features.
Figure 8:
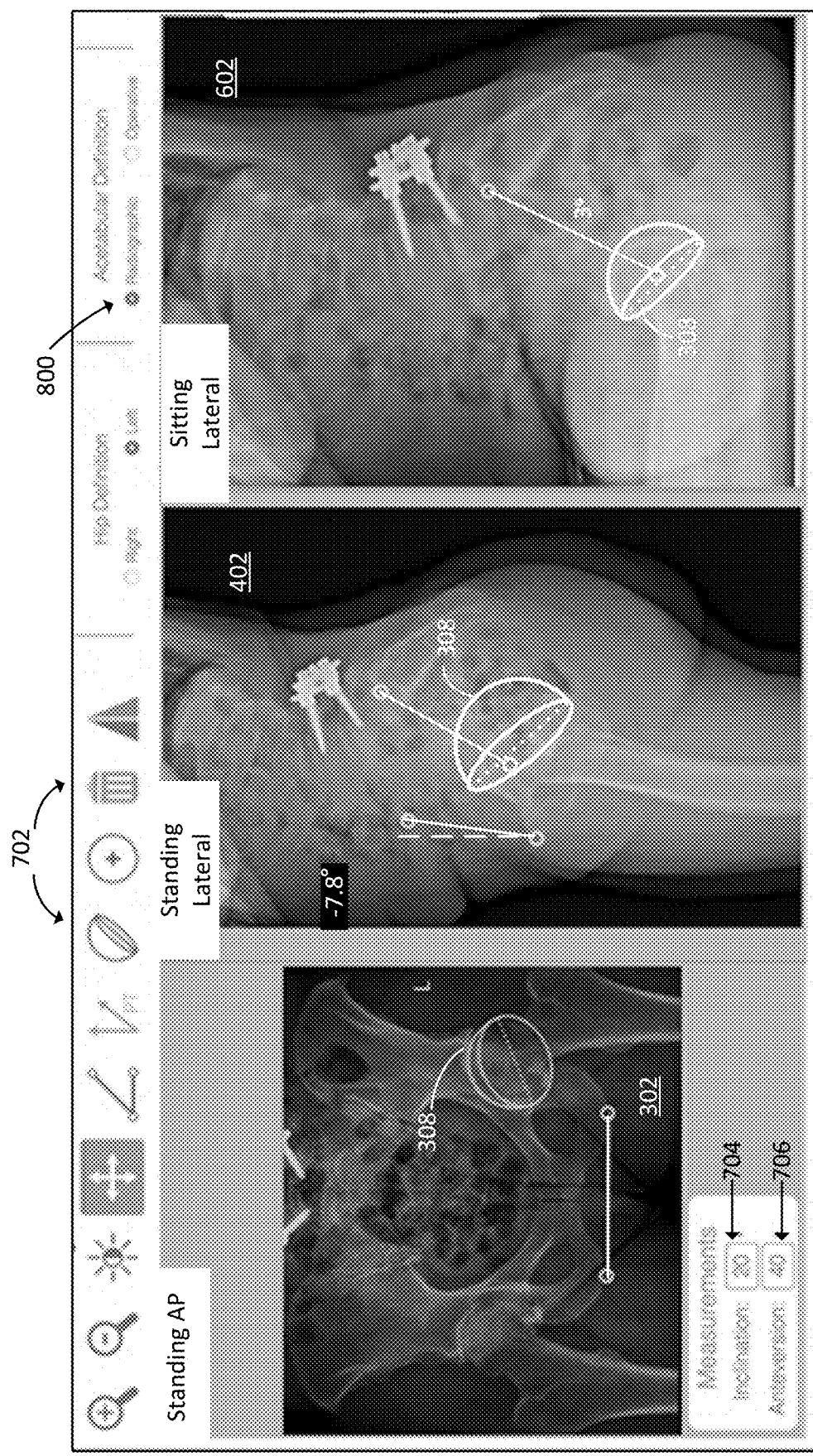

FIGS. 7 and 8 illustrate a GUI showing multiple images (e.g. x-rays, MRI, EOS or other modalities) of a same anatomy simultaneously where the GUI is configured to receive input to define coordinates from positions on the screen that are associated to positions on an anatomy, among other features of the GUI.

More particularly, FIG. 7 shows a GUI 700 to present three x-rays 302, 402 and 602 simultaneously comprising respectively a standing AP view, a standing lateral view and a sitting lateral view. GUI 700 shows controls 702 along a top edge, for example, to zoom in or out, adjust display properties such as contrast and brightness, adjust or scroll the image in the display, input various coordinates, choose between left and right hip (anatomy) and choose between radiographic and operative definition settings.

The computing unit determines the spatial transformations between all three images. In instances where the image acquisition method provides known information about the spatial transformations, this known information may be used in the calculation. Examples of known information include any combination of the following:

AP view is perpendicular to lateral view
AP and or lateral views are aligned to coronal and/or sagittal anatomical planes
The direction of gravity projects onto the y-axis of the resulting images
The projection and/or distortion models of the imaging equipment Computing the spatial transformations may utilize the art of image registration, in which corresponding common features across multiple images are identified, and provided to a solving algorithm, where the solving algorithm determines spatial transformations based on 3D rotations and translations. For example, a spatial transformation may be computed between an AP and lateral pelvis x-ray by identifying at least 3 pairs of corresponding landmarks on each image (such as one ASIS, the pubis, and the inferior point of the sacrum). A coordinate frame may be generated based on the landmarks in each image, and the transformation between the two coordinate frames may be computed as the spatial transformation between both images. In another example, a vector common to two images may be used in the computation of the spatial transformation.

Computing spatial transformations may include a combination of any of the methods described herein as well.

Image registration may utilize 3D information about the anatomical structure of interest (e.g. the pelvis). The 3D information about the anatomical structure may be based on a patient scan (e.g. a segmented pelvis derived from a CT scan). The 3D information may be based on a generic patient template, optionally modified for a patient's parameters such as: height, weight, BMI, sex, race, etc.). The 3D information may be used as a constraint in an optimization computation that determines the spatial transformation between two images.

The computing unit may access the 3D model of an implant (e.g. an acetabular cup). The implant model may be generic (i.e. such as a hemisphere representing an acetabular cup), or specific to a design of a commercially available acetabular cup implant (e.g. based off of CAD). The 3D model may be rendered and displayed on each of the three images, as shown in FIG. 7. The implant is rendered for each image according to the reference axes and/or spatial transformations and/or the change in functional position, based on a consistent 3D position relative to the musculoskeletal structure (e.g. the pelvis) in each image. The 3D model may be initially rendered and displayed in a first, or default, position. For THA, the default may be for the cup to be at 40° of inclination and 15° of anteversion (704 and 706 as in FIG. 7), which is the center of a clinically accepted safe zone (See e.g. Lewinnek et al. Dislocations after total hip replacement surgeries, The Journal of Joint and Bone Surgery (JBJS) 1978; Kanawade et al. Predictability of Acetabular Component Angular Change with Postural Shift from Standing to Sitting Position, JBJS 2014; Buckland et al. Acetabular Anteversion Changes Due to Spinal Deformity Correction: Bridging the Gap Between Hip and Spine Surgeons, JBJS 2015).

Alternatively, the default cup angle may result from a computation to minimize impingement and/or dislocation risk (or maximize joint stability through functional patient movements). For example, a computation to minimize impingement and/or dislocation risk may receive the change in functional position data (i.e. the change in pelvic tilt angle), optionally receive other data, such as the desired hip range of motion, and compute a cup angle to be used as the default. The computation may involve computer-implemented simulation, or a look-up table based on clinical research correlating dislocation and/or impingement risk with change in functional cup position. A default cup position may be chosen by shifting cup position within a known safe zone. The cup position may be shifted within the safe zone based on one or more patient-specific attributes. The shift may be based on the correlation of the tile and anteversion. As described further herein below with reference to FIGS. 24-26, 27A and 27B, a safe zone visualization (or more than one) may be rendered and displayed to visually indicate the location of the safe zone (or safe zones) with respect to one or more of the 3 images. Alternatively, or additionally, placement may be based on a patient's sex, height, weight, Body Mass Index, or more.

The computing unit may be responsive to real time changes to the position of the cup (i.e. changes from the default position). For example, a user may drag one or more handles (using a mouse, trackpad, touchscreen, or other input device for the computing unit) associated with the 3D implant rendering to change its position. In another manner, controls relative to the measurements may receive input (e.g. numeric input) to change the value of the measurements (anteversion and inclination) to instruct the GUI to position the cup implant with such measurements.

FIG. 8 is an illustration of the GUI 700 showing a cup implant 308 with a changed position relative to its position in FIG. 7. Changing the position of a cup implant 308 using a control with respect to one of the x-rays automatically updates in all views to maintain a consistent 3D position relative to the musculoskeletal structure. The change in position for an acetabular cup includes the angles of inclination and anteversion. The change in position may optionally include the translational position and/or the size of the rendered implant. Alternatively, the size and translational position may be independently adjusted for each of the three images. Changes made to the position of the implant would preferably be responsive to user input in real time, so that the user doesn't experience frustrating and/or potentially confusing lag.

In FIG. 7 and FIG. 8 there are fields labeled Inclination and Anteversion, which may update in response to a user modifying the position of the rendered implant, and/or may be user-modifiable such that a user could enter a particular cup angle, and the rendering would update accordingly.

In FIG. 7 and FIG. 8, controls 702 illustrate a radio button control 800 to toggle between radiographic and operative definitions of cup angles. The computer implemented method would calculate and display the Inclination and Anteversion measurements according to the respective cup angle definitions (in mathematical terms, this amounts to using a different set of Euler angles to describe a given 3D rotation).

The use of two standing x-ray views from orthogonal perspectives has been described, and is advantageous for simplifying the process of determining the spatial transformations (since the views are orthogonal, and have a common gravity vector (parallel to the vertical image margin in both images) with respect to the anatomical structures). Two x-ray views from different perspectives may be used without the constraint of sharing a common vector, such as gravity. For example, in THA, often AP pelvis x-rays are taken with the patient supine. Likewise, CT scans typically having the patient lying supine during image acquisition. The spatial transformation between the images of different perspectives may be calculated without relying on a common direction of gravity (i.e. as described previously wherein image registration techniques are used to determine the spatial transformation). A computer-implemented method may provide alternative methods for calculating the spatial transformations, where one alternative relies on two different views sharing a common vector (e.g. gravity), and the other alternative does not, but relies instead on matching anatomical landmarks via image registration. The computer-implemented method may receive user input to indicate which of the two alternative methods to use for a given set of images.

The use of more than three images is contemplated. More than two images related by a functional motion may be used. For example, in addition to a sitting and standing lateral image of a pelvis, a flexed-sitting view and/or a step-up view (in which a patient has their contra-lateral leg raised as if they are "stepping up") may be provided. The computer-implemented method may receive the additional functional views, compute the change in functional position parameters (e.g. change in pelvic tilt), compute the respective spatial relationships, and render and display a 3D implant accordingly on each view. The use of additional non-functional views is also contemplated. For example, a supine AP hip x-ray is commonly used in clinical practice. The spatial transformation between this view and the other views may be computed, and the 3D implant may be rendered on this image based on the spatial transformations. In another example, spatial transformation between functional images and a CT scan enables 3D implant overlays on a supine coronal, supine transverse and supine sagittal view.

The computer-implemented method described herein may utilize any 3D implant model, corresponding to the implants of a particular surgery. For example, in a THA, the 3D implant model of a femoral prosthesis (either a generic model, or a manufacturer-specific model) may be used instead of, or in addition to an acetabular cup 3D implant model. In the case of a femoral prosthesis, the musculoskeletal structure associated with this implant is a femur, and reference axes associated with the femur may be identified in the respective medical images. As a result, renderings of both the femur stem and acetabular cup implants may be provided on the x-ray views (e.g. the AP pelvis, the standing lateral x-ray and the sitting lateral x-ray). The version of the femur stem is an important clinical parameter, since it is controllable by the surgeon during a THA (whereas flexion and/or varus angles of the femur stem are generally enforced by the anatomy). The version of the femur stem may be a parameter representing the position of the femur stem (analogous to Inclination and Anteversion for an acetabular cup implant). The position of the femur stem may be updated in real time by invoking a processor executing computer instructions via clicking on handles associated with the 3D rendering and/or manually entering values into a field for femur stem position. As with the previously-described acetabular implant position, the position of the femur stem rendering may update in real time on each image based on a consistent 3D position relative to the femur.

In THA, digital templating (aka implant sizing) is commonly performed to predict implant sizes, and determine an expected position of the prostheses. Digital templating is typically performed on an AP pelvis or AP hip x-ray. The computer-implemented method herein may implement a templating module, so that a surgeon has a single software interface to perform their pre-operative planning. Alternatively, the computer-implemented method may receive templating information to influence how or where the implant is rendered on the image. For example, the templating information may include: implant size, implant make/model, image scaling factor, implant translational position. When rendering the 3D implant on the respective images, they may be rendered to achieve consistency with the templating information (e.g. the center and size of an acetabular prosthesis as templated causes the 3D model rendering to be centered at the same location in the image, with the same size).

The computer-implemented method described herein may be used for pre-surgical planning, or post-surgical validation, or both. Where both pre-operative and post-surgical images are used, changes between the pre- and post-references axes and change in tilt parameters may be calculated and provided for display to a user (for example, to quantify how the change in pelvic tilt during functional motions changed as a result of the surgical procedure).

The computer-implemented method may be implemented using a computing device (sometimes referenced as a computing unit). Representative but non-limiting examples include a laptop, PC, workstation, server, tablet and smartphone.

Figure 9:
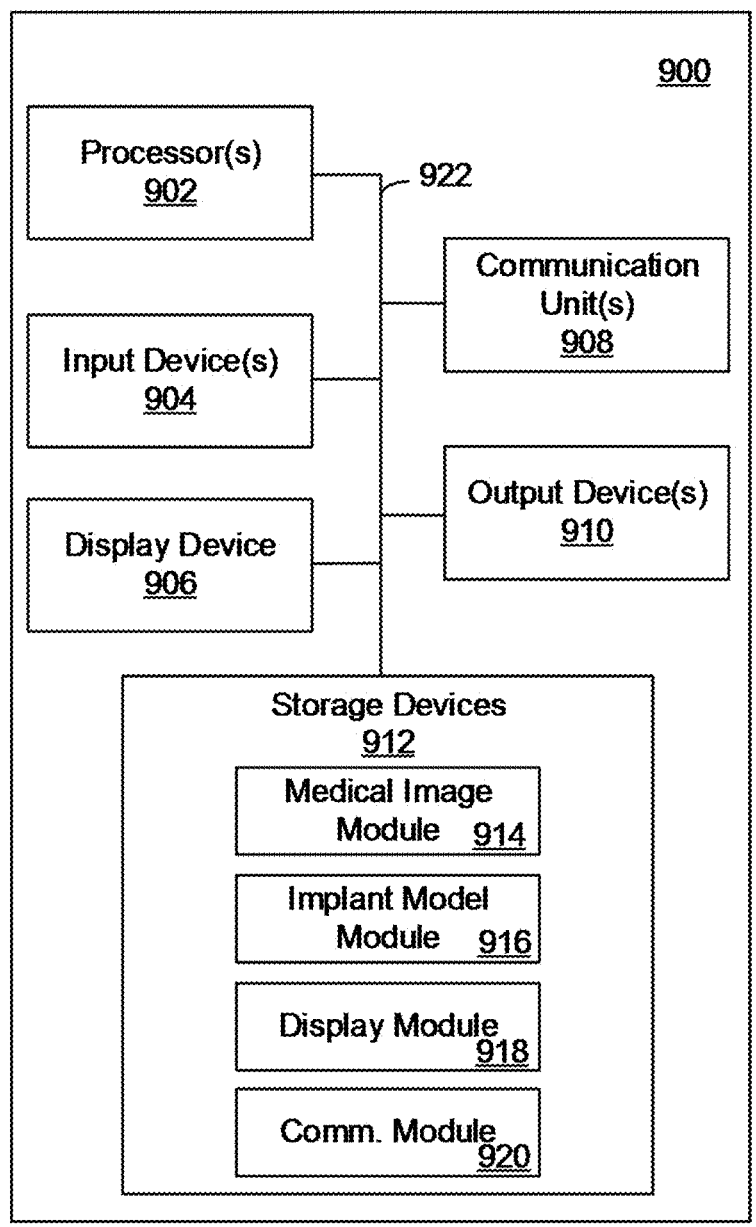
FIG. 9 is a block diagram of a computing device configured in accordance with the teachings herein.

FIG. 9 is a diagram illustrating in block form an example computing device (e.g. 900), in accordance with one or more aspects of the present disclosure, for example, to provide a computing device to perform to any one of the method aspects described herein. Computing device 900 comprises one or more processors 902, one or more input devices 904, a display device 906, one or more communication units 908 and one or more output devices 910. Computing device 900 also includes one or more storage devices 912 storing one or more modules (e.g. as software) such as medical image module 914, implant model module 916, display module 218 and communication module 920. Communication channels (e.g. 922) may couple each of the components 902-920 for inter-component communications, whether communicatively, physically and/or operatively. In some examples, communication channels 922 may include a system bus, a network connection, an inter-process communication data structure, or any other method for communicating data.

Figure 2A:
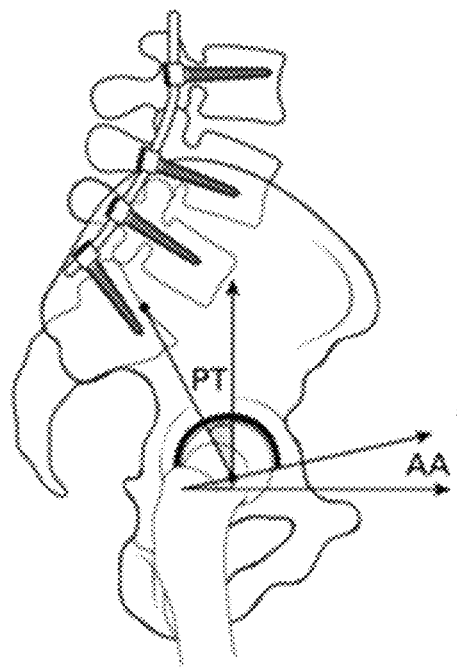
FIGS. 2A and 2B illustrate abnormal pelvic movement from the standing to the sitting position in accordance with the prior art.
Figure 2B:
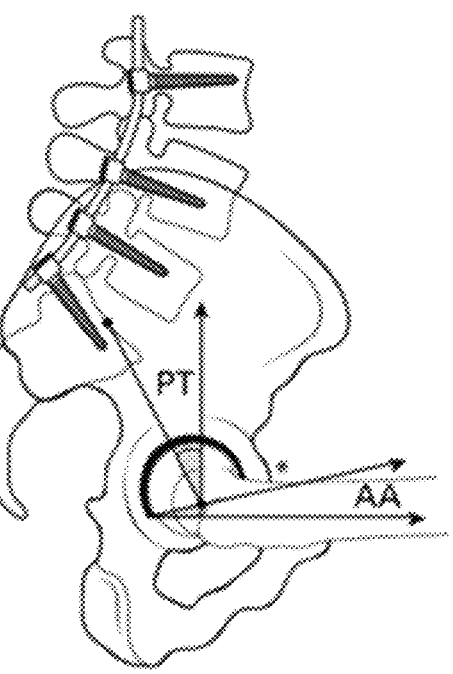

One or more processors 902 may implement functionality and/or execute instructions within computing device 900. For example, processors 902 may be configured to receive instructions and/or data from storage devices 912 to execute the functionality of the modules shown in FIG. 2, among others (e.g. operating system, other applications, etc.) Computing device 900 may store data/information to storage devices 912. Computing device 900 may be coupled to external storage devices (not shown), whether they are located closely or remotely from device 900. For example, remote storage devices (not shown) may be accessible via a server or other computing device to receive images of a patient. The images may be copied and stored locally in storage devices 912 or in external devices, such as for use during preoperative planning or postoperative review.

One or more communication units 908 may communicate with external devices such as servers (not shown), etc. via one or more networks (not shown) by transmitting and/or receiving network signals on the one or more networks. The communication units may include various antennae and/or network interface cards, etc. for wireless and/or wired communications.

Input and output devices may include any of one or more buttons, switches, pointing devices, cameras, a keyboard, a microphone, one or more sensors (e.g. biometric, etc.) a speaker, a bell, one or more lights, etc. One or more of same may be coupled via a universal serial bus (USB) or other communication channel (e.g. 922). In the present example, computing device 900 comprises a display device 906. In other examples, computing device is coupled to an external display device (not shown). Of course device 900 may have a display device 906 and also be coupled to an external display device. The display device may be configured to provide input to device 900 such as via a touch screen, etc.

The one or more storage devices 912 may store instructions and/or data for processing during operation of computing device 900. The one or more storage devices may take different forms and/or configurations, for example, as short-term memory or long-term memory. Storage devices 912 may be configured for short-term storage of information as volatile memory, which does not retain stored contents when power is removed. Volatile memory examples include random access memory (RAM), dynamic random access memory (DRAM), static random access memory (SRAM), etc. Storage devices 912, in some examples, also include one or more computer-readable storage media, for example, to store larger amounts of information than volatile memory and/or to store such information for long term, retaining information when power is removed. Non-volatile memory examples include magnetic hard discs, optical discs, floppy discs, flash memories, or forms of electrically programmable memory (EPROM) or electrically erasable and programmable (EEPROM) memory.

Medical image module 914 may be configured to receive and work with the various forms of medical images as described herein. For example, it may be configured to determine various axis and transformations, etc. and prepare image data therefrom for display via display module 918. Implant model module 916 may be configured to receive implant model data and work with it to enable the renderings and movement/manipulation of the renderings via input from the one or more of the input devices as described herein. Display module 918 may display images from modules 914 and 916. It is understood that operations may not fall exactly within the modules 914-920 of FIG. 9 such that one module may assist with the functionality of another. Additional modules may be stored (not shown).

Figure 10:
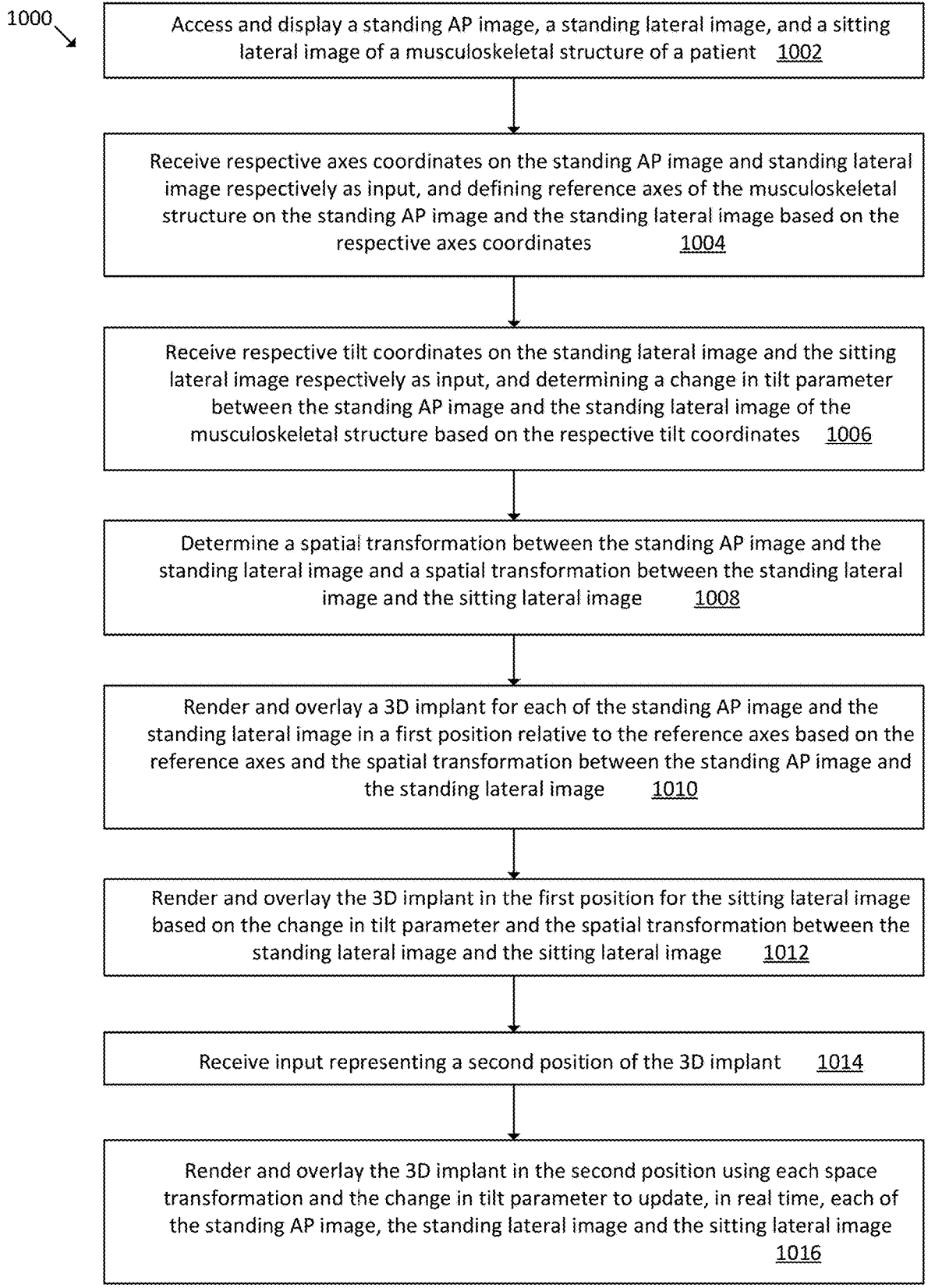

FIG. 10 is a flowchart showing operations 1000 of a computer implemented method, such as may be implemented by computing device 900. At 1002 operations access and display multiple images showing anatomy for example, a standing AP image, a standing lateral image, and a sitting lateral image of a musculoskeletal structure of a patient. At 1004 operations receive respective axes coordinates on two x-rays from different points of view (e.g. the standing AP image and standing lateral image respectively) as input, and define reference axes of the musculoskeletal structure on the respective x-rays (e.g. standing AP image and the standing lateral image) based on the respective axes coordinates.

At 1006 operations receive respective tilt coordinates (e.g. on the standing lateral image and the sitting lateral image respectively) as input, and determine a change in tilt parameter (between the standing AP image and the standing lateral image) of the musculoskeletal structure based on the respective tilt coordinates.

At 1008 operations determine relevant respective spatial transformations between pairs of x-rays (e.g. between pairs of images in different points of view and pairs of images in a same point of view but showing different positions of the anatomy) For example, operations may determine a spatial transformation between the standing AP image and the standing lateral image and a spatial transformation between the standing lateral image and the sitting lateral image.

Operations render and overlay a 3D implant for each of the x-rays using the reference axes, spatial transformations and change in tilt parameter. For example, at 1010 operations render and overlay a 3D implant for the standing AP image and the standing lateral image in a first position relative to the reference axes based on the reference axes and the spatial transformation between the standing AP image and the standing lateral image. At 1012 operations render and overlay a 3D implant in the first position for the sitting lateral image based on the change in tilt parameter and the spatial transformation between the standing lateral image and the sitting lateral image.

Operations may receive input to move the implant to a second position and update a rendering and overlay of the implant to the second position in each of the x-rays, e.g. in real time. At 1014 operations receive input representing a second position of the 3D implant; and, at 1016, render and overlay the 3D implant in the second position using each space transformation and the change in tilt parameter to update, in real time, each of the standing AP image, the standing lateral image and the sitting lateral image.

It is understood that the images may be from any of the following modalities: x-ray, CT, MRI, EOS. The computer implemented method may display the change in tilt parameter (and any of the reference axes or other measurements). Determining spatial transformations may comprise one or more of: performing computations based at least in part on the received coordinates; performing computations based on corresponding common features between received images; and performing computations based on known image acquisition spatial information.

FIG. 11 is a flowchart of operations 1100 of a computing device such as computing device 900. At 1102 operations access and display at least three images of a musculoskeletal structure of a patient, where one pair of images are of different views of a first position, and another pair of images are of the same view in different functional positions. At 1104 operations define reference axes of the musculoskeletal structure on at least two images, based on user input. At 1106 operations determine a positional change parameter of the musculoskeletal structure based on the two images of a common view in different functional positions, the positional change parameter representing the positional change of the patient between the functional positions. At 1108 operations determining spatial transformations between the images. At 1110 operations render and overlay a 3D implant for each image in a first position relative to the reference axes, and according to the respective spatial transformations, on the respective images. At 1112 operations receive input representing a second position, and, at 1114, update, in at least near real time, the render and overlay accordingly for each image.

Co-Registered Image Views

Multiple combinations of medical images can be co-registered within the computing system (i.e. in accordance with the computer implemented method) to provide information about the relationships of the image coordinate systems for the purpose of cup visualization across the coordinate systems and relative to the different views. These medical images can include Standing AP, Standing Lateral, Sitting Lateral and Supine AP image views.

Standing AP to Standing Lateral

The Standing AP and Standing Lateral images may be co-registered by design/assumption. The computer implemented method assumes that the vertical axis of both images are parallel, and the horizontal axes of the images are 90 degrees offset from each other. This may be achieved with EOS imaging system (https://www.eos-imaging.com/), or with conventional radiographs and careful patient positioning during image acquisition. A patient may be directed to rotate 90°, pelvic landmarks may be used, a positioning jig may be used, etc.).

FIGS. 12A and 12B are EOS images 1200, 1202 of an anatomy from two views showing reference axes in each view. In both EOS images 1200, 1202, the vertical axes 1204, 1206 are parallel. The horizontal axis 1208 of the AP image (EOS image 1200) is assumed to be perpendicular to the lateral image plane, and the horizontal axis 1210 of the lateral image (EOS image 1202) is assumed to be perpendicular to the AP image plane.

Standing Lateral to Sitting Lateral

To co-register the standing lateral to sitting images, the computer implemented method assumes that the pelvises in both lateral images have only rotated in the image plane, and can be measured by identical measuring pelvic landmarks on both images. One such landmark that could be used is the sacral slope (angle of the superior aspect of the sacrum).

Figure 13:
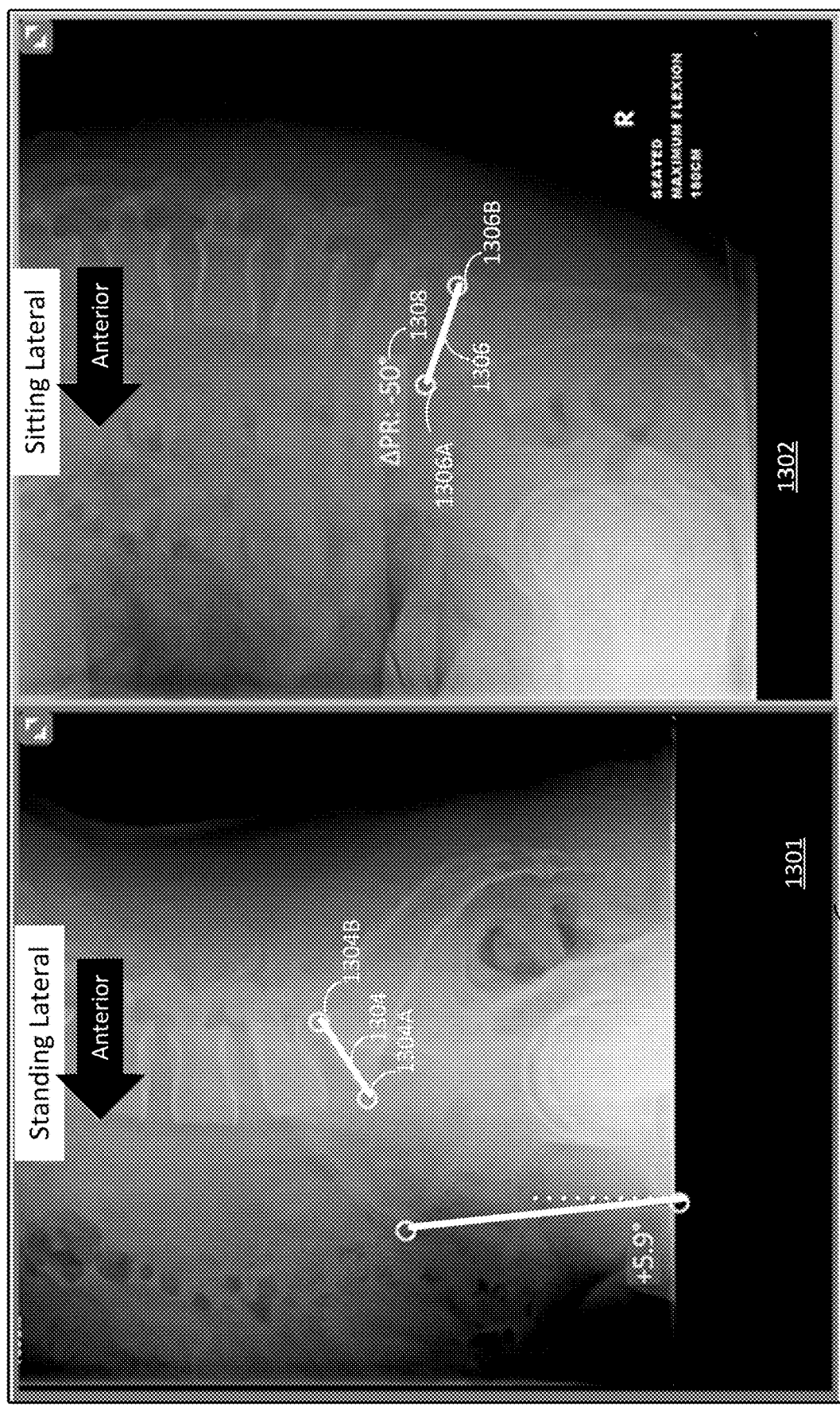
FIGS. 13 and 14 are illustrations of a portion of a respective GUI 1300 showing two images and enabled to receive input of coordinates and determine (e.g. compute) clinically relevant values therefrom, among other features.

FIG. 13 is a portion of a GUI 1300 showing two images 1301 and 1302. Input has been received to mark coordinates to indicate respective slopes. The shorter lines 1304 and 1306 between the pairs of round handles (e.g. 1304A, 1304B and 1306A, 1306B) are used to measure the sacral slope of the pelvis in the two images 1300 and 1302. The difference in the angle of the sacral slope is −50 degrees (50 degrees of posterior rotation) and is displayed (1308).

Other landmarks can be used (e.g. hip center to operative ASIS, or pubis to ASIS) as long as the same reference line is used on both images.

Standing AP to Supine AP

To co-register the two AP images, operations of the computer implemented method calculate to predict a change in Pelvic Tilt between two AP radiographs such as by crafting and using a model. On each image several bony landmarks are measured—a distance from the top of the pubis to the trans-ischial line, and a pelvic outlet diameter. 3D models, and synthetic x-rays with known pelvic tilts, were employed to use these pelvic landmarks to model change in pelvic tilt. Thus a look up table (e.g. a nomogram) was defined using representative population data.

The model is a linear model which calculates pelvic tilt for one image (pelvic tilt relative to the image plane), and the difference in pelvic tilt is reported:

$$pt = \left(\frac{PSTI}{POD}\right) * m + b$$

Where PSTI is the line from the top of the pubis (PUBIS) to the trans ischial line (TI), POD is the pelvic outlet diameter, and m and b are the coefficients of the model, which are gender specific.

One method of determining this model is to collect both known (i.e. measured) model inputs (e.g. PSTI and POD) and known (i.e. measured) model outputs (e.g. PT) from a representative set of sample data (e.g. a statistically significant quantity of radiographs with representative demographics (gender, race, age, BMI)). With a paired list of known inputs and outputs to a model, it is then possible to determine the model parameters (e.g. m and b) using any linear or non-linear optimization method. The example described here is a linear model with two inputs (PSTI and POD) and one output (PT), but the model may also be non-linear with fewer or greater numbers of inputs.

In accordance with the method, the difference in pelvic tilt (PTD) (e.g. 19°) may be displayed, such as via a GUI.

Figure 14:
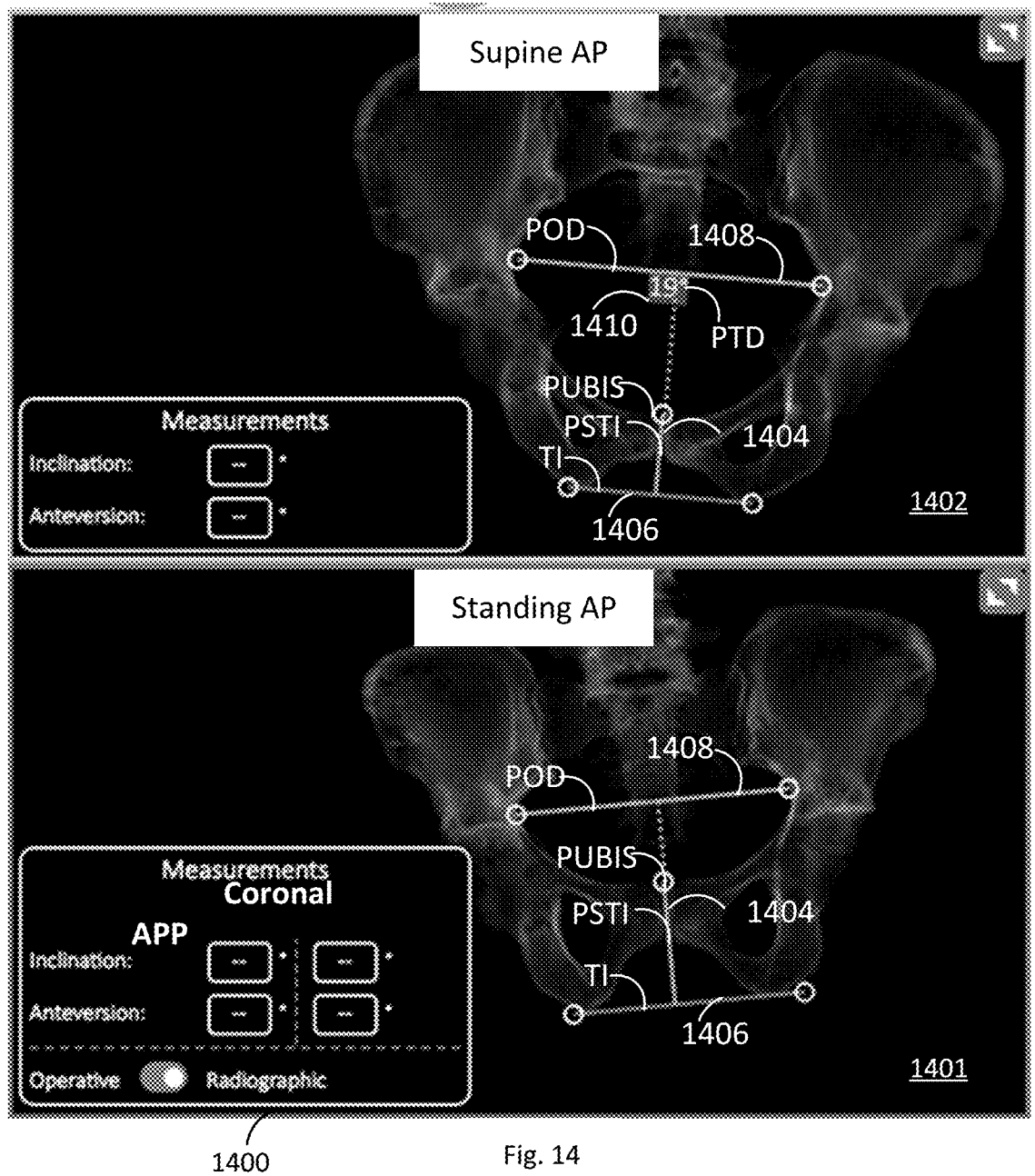

With reference to FIG. 14 there is shown a portion of a GUI 1400 showing two images 1401 and 1402, where on both images, the length of the line 1404 from the top of the pubis to the trans-ischial line 1406 is measured and scaled by the pelvic outlet diameter (line 1408). This ratio is plugged into a model developed to measure pelvic tilt. This example shows (at GUI element 1410) a pelvic tilt of 19 degrees in the anterior direction.

Other landmarks may be used, for example, the "teardrop" line (not illustrated with a line in FIG. 14) may be used instead of the trans-ischial line and a model developed.

Figure 15:
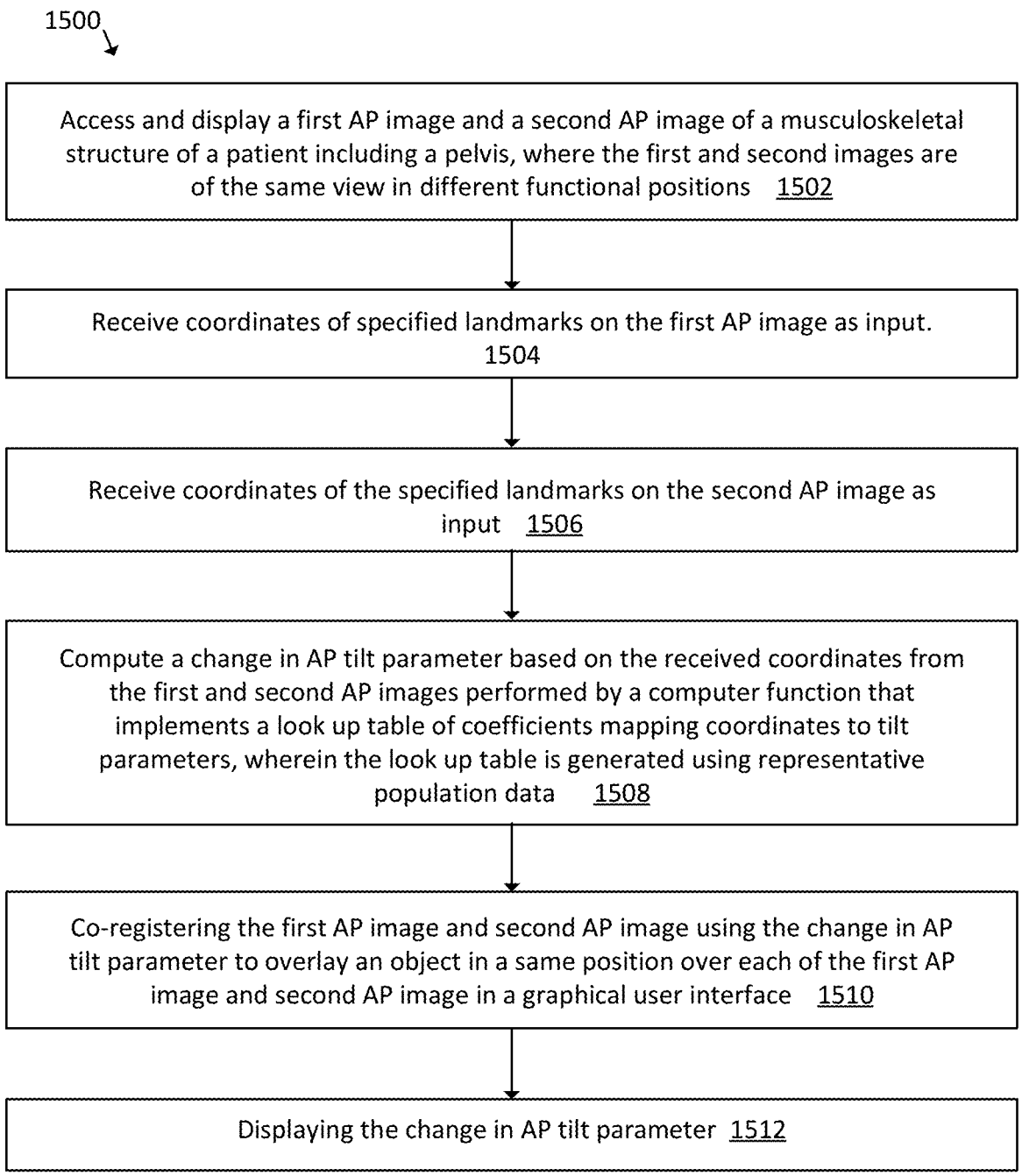
FIG. 15 is a flowchart of operations of a computing device in accordance with the teachings herein.

FIG. 15 is a flowchart of operations 1500 for a computing device such as computing device 900.

At 1502 operations access and display a first AP image and a second AP image of a musculoskeletal structure of a patient including a pelvis, where the first and second images are of the same view in different functional positions. At 1504 operations receive coordinates of specified landmarks on the first AP image as input. At 1506 operations receive coordinates of the specified landmarks on the second AP image as input. At 1508 operations compute a change in AP tilt parameter based on the received coordinates from the first and second AP images using a computer function that implements a look up table of coefficients mapping coordinates to tilt parameters, wherein the look up table is generated using representative population data. At 1510 operations co-registering the first AP image and second AP image using the change in AP tilt parameter to overlay an object in a same position over each of the first AP image and second AP image in a graphical user interface. The change in AP tilt parameter may be provided for display (1512).

The computer implemented method may further comprise rendering a 3D implant (an example of an object) and overlaying it for each of the first AP image and the second AP image in a first position based on reference axes and the change in tilt parameter. The computer implemented method may further comprise displaying numerical values indicating the first position (e.g. angles relative to the reference axes).

The 3D implant may be an acetabular cup and the musculoskeletal structure may be a pelvis of a patient. The numerical values may be inclination and anteversion, and wherein inclination is relative to a medial-lateral reference axis, and anteversion is relative to the plane of the x-ray for each image. In this computer implemented method, the first AP image may be a standing AP Pelvis x-ray, and the second AP image may be a supine Pelvis x-ray. The specified landmarks of the pelvis are the inferior bilateral ischial tuberosities, the pubic symphysis, and the lateral-most points along the pelvic brim.

Computation of the of the AP tilt parameter may be based on population data that is different for males and females, and the method may include receiving input to indicate the gender of the patient.

The computer implemented method regarding the AP tilt parameter may be performed in conjunction with other computer implemented methods described herein. For example it may be performed following a computer implemented method to determine spatial transformations between pairs of images (e.g. a pair of images comprising different views of a same position or a pair of images comprising same views of different functional positions) using references axes determined for such images and rendering and displaying a 3D implant over the images using the spatial transformation(s) as applicable.

Functional to APP

Figure 16B:
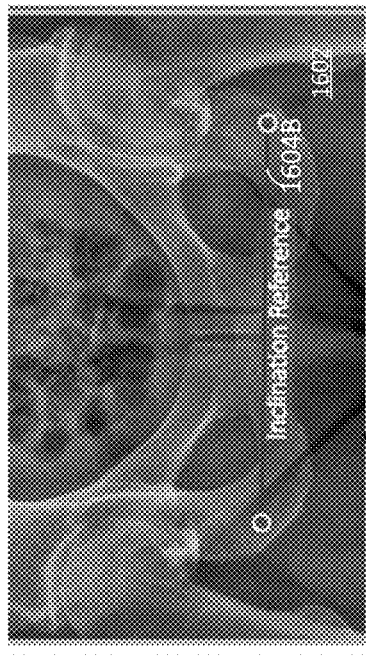
FIGS. 16A-16C are illustrations of portions or respective GUIs showing respective images and enabled to receive input of coordinates and determine (e.g. compute) clinically relevant values therefrom, among other features.
Figure 16C:
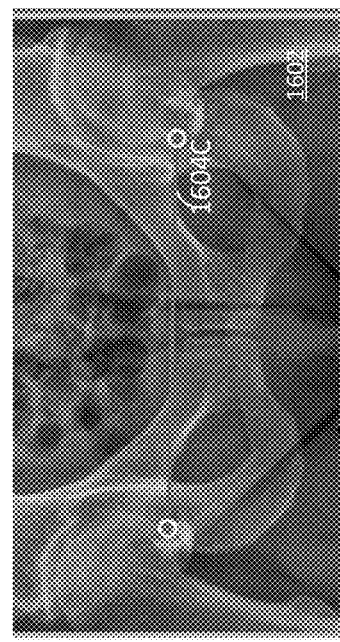
Figure 16A:
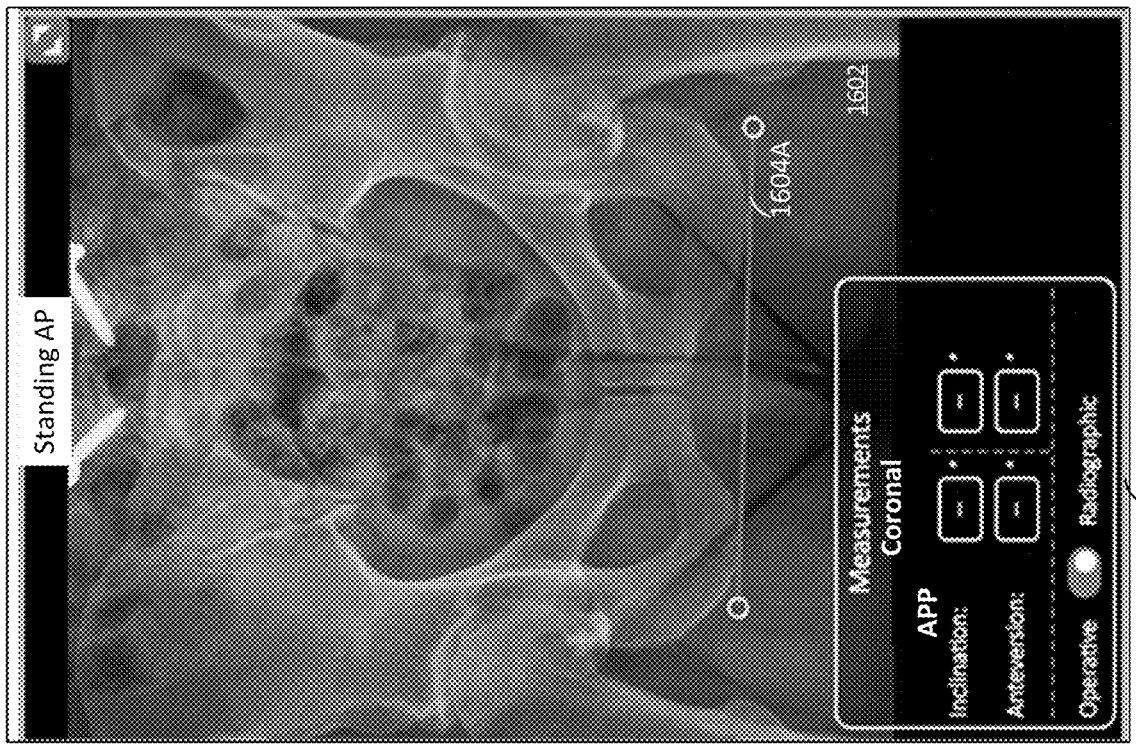

FIGS. 16A-16C are illustrations of portions of a GUI 1600A, 1600B and 1600C showing an image 1602 and enabled to receive input of coordinates and determine (e.g. compute) clinically relevant values therefrom, among other features. Each of FIGS. 16A-16C show a standing AP image (image 1602) where FIG. 16A shows a larger portion thereof and FIGS. 16B-16C show a smaller portion thereof for ease of illustration.

Figure 17:
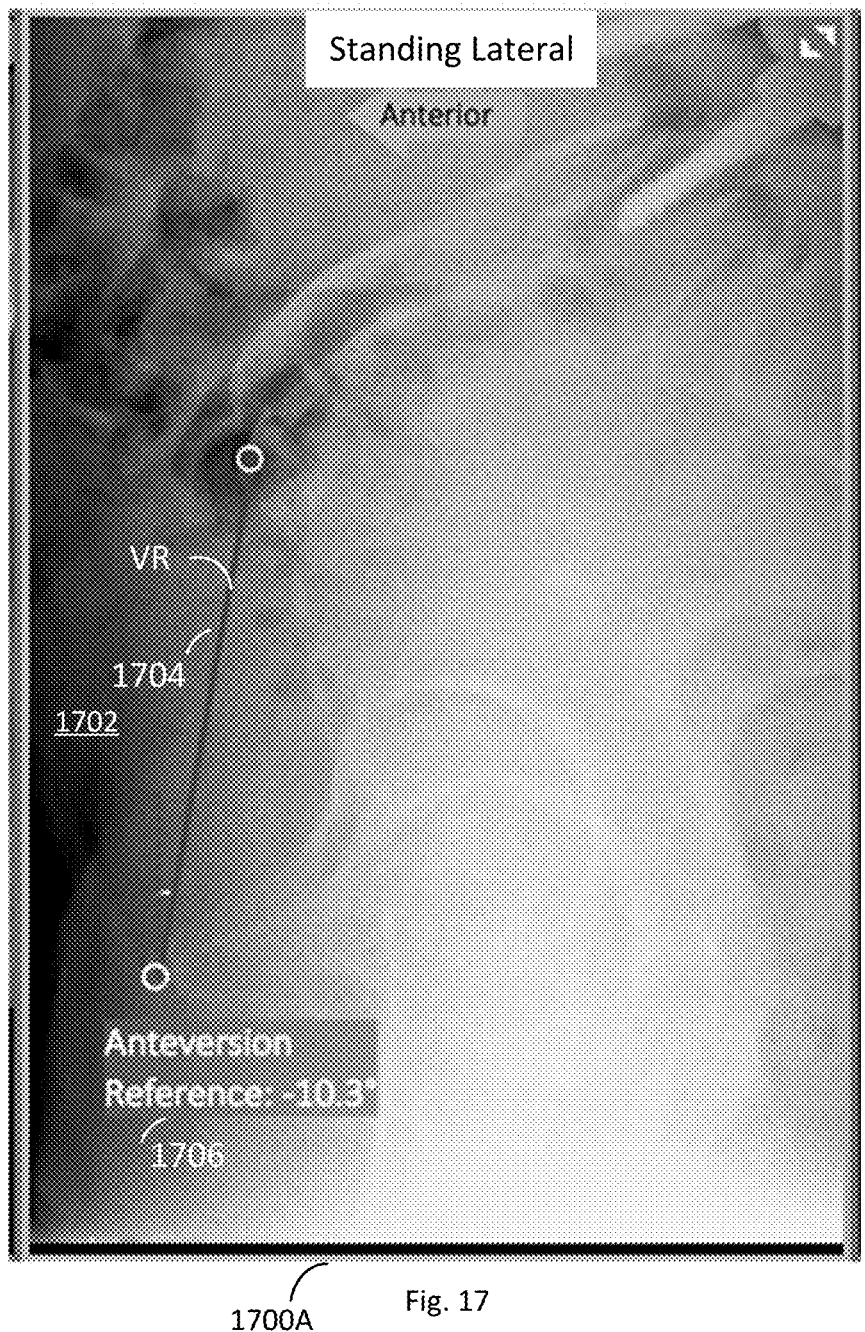
FIG. 17 is an illustration of a portion of GUI showing one of the images that may be displayed by the GUI enabled to receive input of coordinates and determine (e.g. compute) clinically relevant values therefrom, among other features.

In accordance with a computer implemented method, to calculate the registration between the functional position (standing coronal), and the APP (a commonly accepted pelvic reference frame) there is measured a horizontal reference 1604A, 1604B and 1604C (inclination reference) in the standing AP image, and a vertical reference (anteversion reference) in the standing lateral image (See FIG. 17).

The horizontal reference can be any number of clinically accepted landmarks. It can be the inter-ischial line, the teardrop line, the line between the bottom of the obturator foramens, or any other set of landmarks the user deems appropriate for a horizontal reference. Examples of the different horizontal references (1604A, 1604B and 1604C) are shown in FIGS. 16A-16C where a Trans/Inter Ischial line is shown in FIG. 16A (left), a bottom of obturator foramens is shown in FIG. 16B (top right), and a teardrop line in FIG. 16C (bottom right).

With reference to FIG. 17 showing a portion of a GUI 1700 showing an image 1702 comprising a standing lateral image, the vertical reference 1704 is always the line from the pubic symphysis to the ASIS points. In the case where the ASIS points are not superimposed, the line can bisect the two ASIS points. As illustrated in FIG. 17, the vertical reference line (VR) is shown from the pubis (bottom white circle), and bisecting the two ASIS points (top white circle). The measured tilt of the pelvis, relative to the standing coronal plane, is −10.3 degrees (posterior pelvic tilt) as shown in the graphical element 1706.

Cup Visualization on Co-Registered Views

When all views have been co-registered, a visual representation of a cup implant can be simultaneously viewed on any or all images, and reported in all measurement planes.

Figure 18:
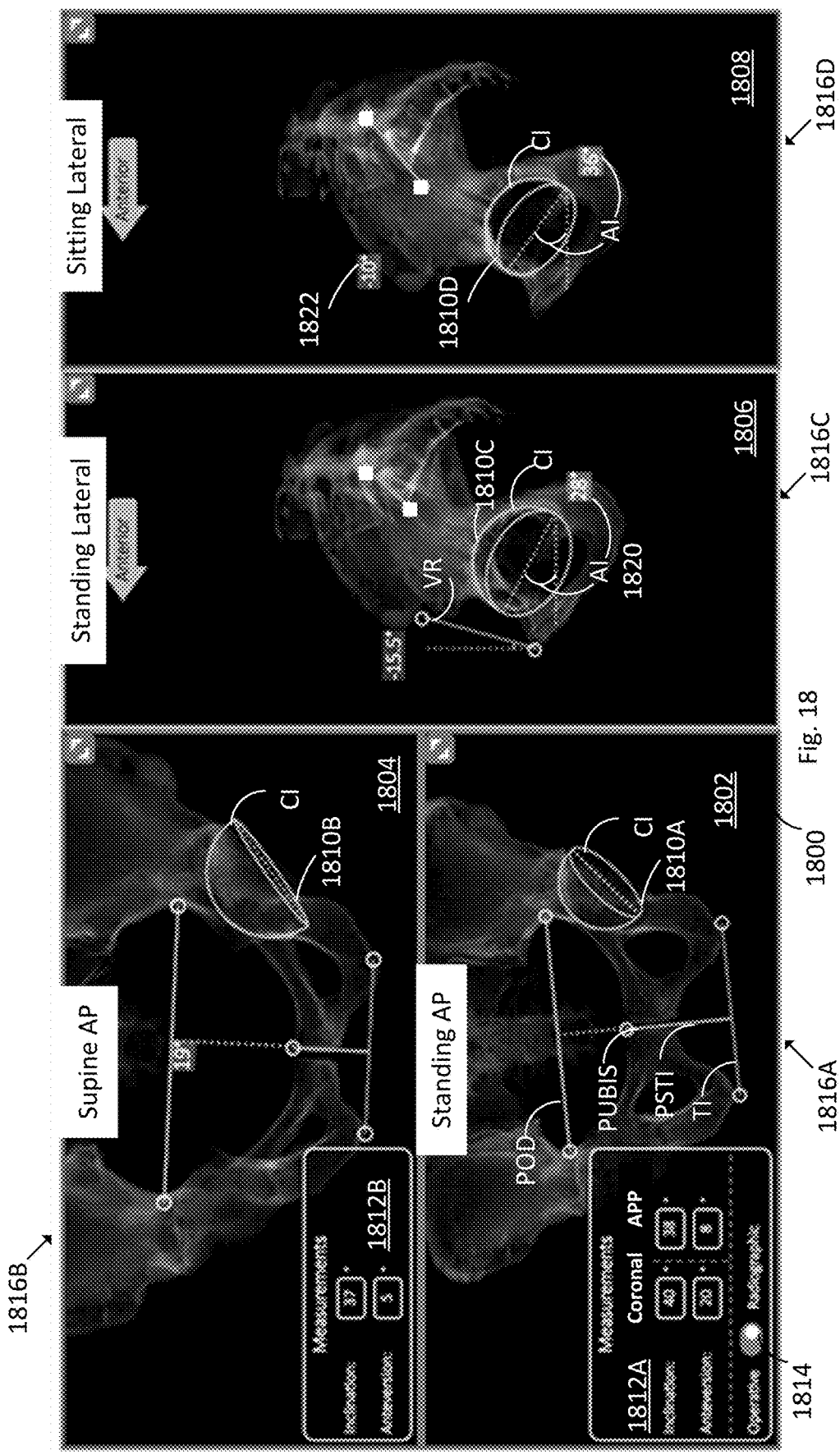
FIG. 18 is an illustration of a portion of a GUI showing four respective images enabled to receive input of coordinates and determine (e.g. compute) clinically relevant values therefrom, among other features

FIG. 18 is an illustration of a portion of a GUI 1800 having similar functions and features of the other GUIs and comprising an instance where all four images 1802, 1804, 1806 and 1808 are present and a cup overlay 1810 (CI) is visualized. In this case there are visualizations on all four images, and they show what the shape of the cup as if there had been a cup present during the imaging. There are also measurements 1812A and 1812B reported in various clinically relevant coordinate systems, including the standing coronal (1812A), and supine coronal reference frames (1812B), as well as the APP reference frame (1812A).

These cup visualizations 1810A, 18106, 1810C and 1810D and reported angular measurements (1812A, 1812B) are linked. Changing any one of the visualizations (i.e. a position of one of the cup implants 1810A, 18106, 1810C and 1810D over any one of the images 1802, 1804, 1806 or 1808) adjusts all the other visualizations, as well as the reported measurements. If the visualization 1810C of the cup implant is changed, then visualizations 1810A, 18106 and 1810D are changed automatically.

Figure 19:
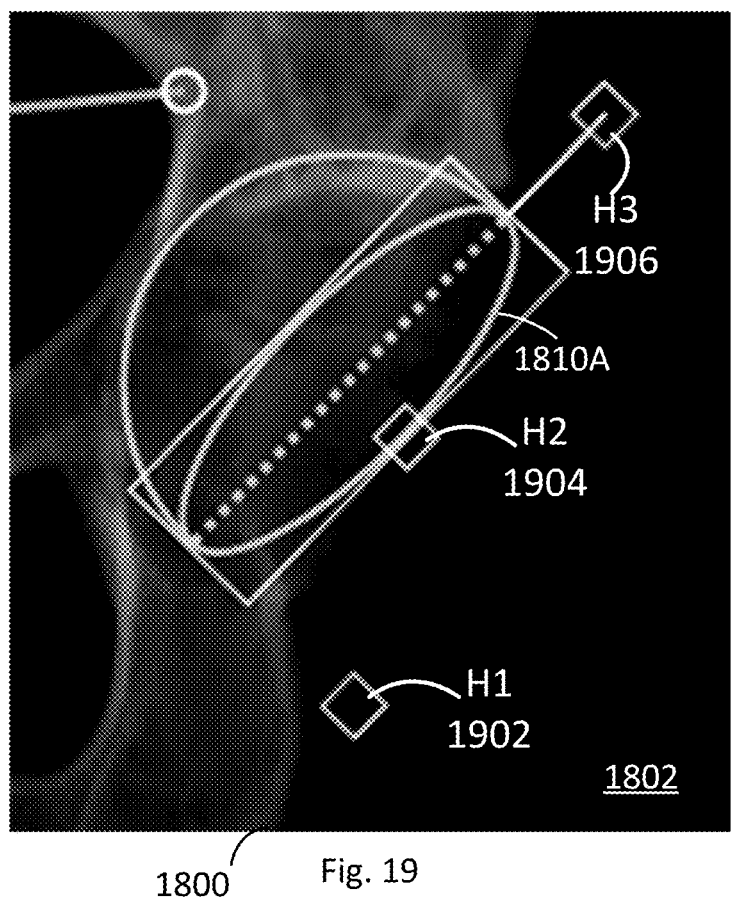
FIG. 19 is an enlarged view of a portion of the GUI of FIG. 18 in which a control is invoked.

FIG. 19 illustrates an enlarged portion of the GUI 1800 showing cup implant 1810A and in which the input has been received to select or invoke a control therefor (e.g. by selecting the cup implant in the GUI 1800) to change the position of the cup implant. In accordance with the computer implemented method the GUI may be configured so that the cup overlay CI in any of the image views can be adjusted (moved) using handles on the respective objects (FIG. 19). Using the handles in one image moves the CI accordingly in all images, preferably in near real time to avoid any lag or negative user experience. The cup implant can be adjusted in size (bottom floating handle H1 1902), anteversion (middle handle H2 1904), or inclination (top handle H3 1906).

Alternatively or in addition, the cup overlay in the images may be adjusted (moved) by inputting new values into the measurement text boxes to change an angle. The CI position is then adjusted in all images using the image co-registrations.

Multiple Displays of Cup Angles in Different Reference Frames

All the visualizations and measurements displayed (e.g. in FIG. 18) represent a single cup CI placed at a given orientation in the pelvis, and represented in various coordinate systems using the co-registrations described above.

The inclination and anteversion angular measurements can be reported using two common definitions, Radiographic, and Operative, using a toggle switch 1814 (in the bottom left). Changing the angle representation does not affect the visual representation. That is, toggling the definition changes the text comprising the specific measurements shown on the screen, but not the visualization. Input to change the specific measurements (in either definition) updates the visualization according to medically accepted relationships.

In the different image panes 1816A, 1816B, 1816C and 1816D, the cup may be visualized as a projection onto the image plane to help the user visually align the cup. The user also uses cup angles to determine proper cup positioning. These angles can be calculated according to multiple reference frames, such as the standing coronal, supine coronal, and anterior pelvic planes. These measurements can all be displayed simultaneously as shown in measurement display text boxes in FIG. 18.

Ante-Inclination Lateral

Ante-inclination (AI 1820) is the angle the major axis of a cup projected onto a lateral image makes with the horizontal margin of that image. The measurement of AI 1820 is invariant to the selected definition of angular measurements and is only determined using the current cup visualization position. The measurement can be seen in FIG. 18 as graphical element 1822. The ante-inclination in various positions has been shown to correlate with various clinically relevant considerations, such as dislocations, or the stiffness of the spine.

Figure 20:
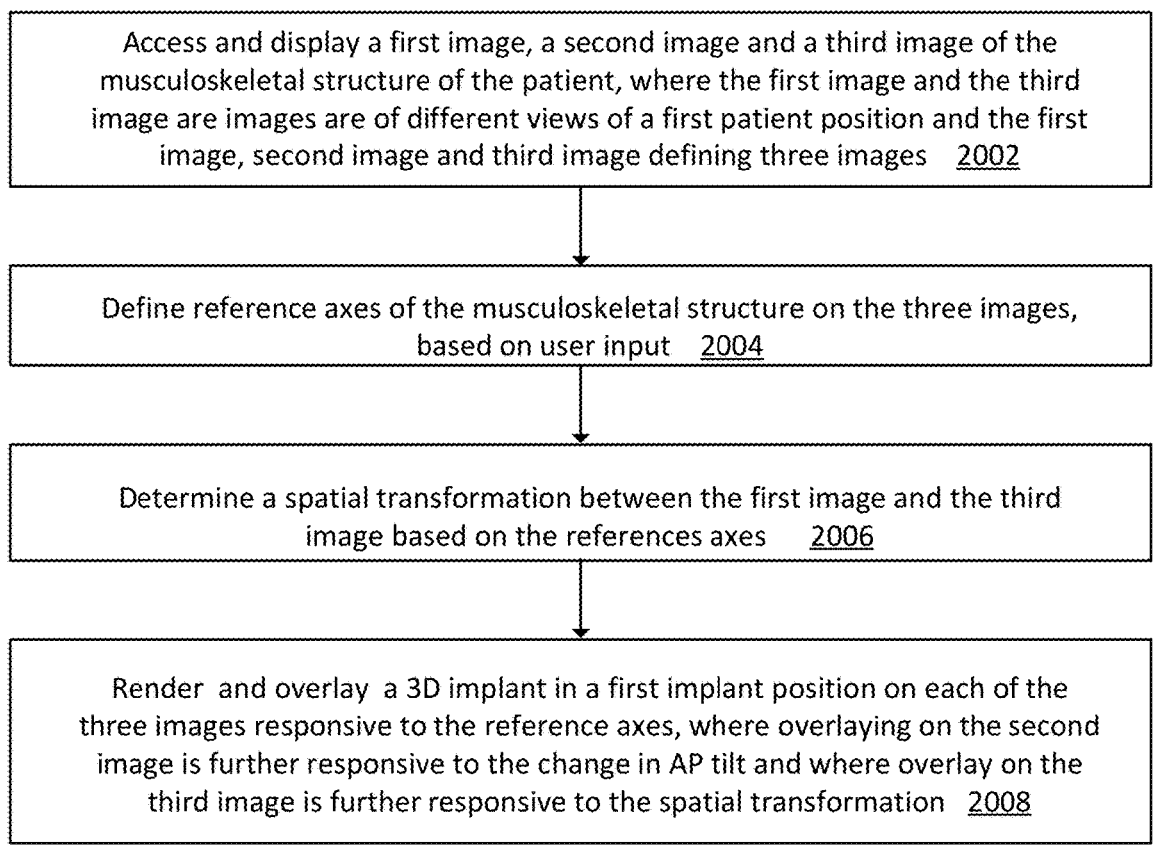
FIGS. 20-22 are flowcharts of operations of a computing device in accordance with the teachings herein.

FIG. 20 is a flowchart of operations 2000 for a computing device such as computing device 900. The operations may provide a method to render and overlay a 3D implant in 3 images simultaneously. The method may be performed after determining a change in AP tilt such as previously described with reference to FIG. 15, or in another manner.

At 2002, operations access and display a first image, a second image and a third image of the musculoskeletal structure of the patient, where the first image and the third image are images are of different views of a first patient position and together the first image, the second image and the third image define three images. At 2004, operations define reference axes of the musculoskeletal structure on the three images, based on user input. At 2006 operations determine a spatial transformation between the first image and the third image based on the references axes. At 2008 operations render and overlay a 3D implant in a first implant position on each of the three images responsive to the reference axes, where overlaying on the second image is further responsive to the change in AP tilt and where overlay on the third image is further responsive to the spatial transformation.

The operations 2000 may comprise receiving input to overlay the 3D implant in a second implant position and updating the overlaying of the 3D implant in the second implant position in the three images responsive respectively, to the change in AP tilt and the spatial transformation.

Figure 21:
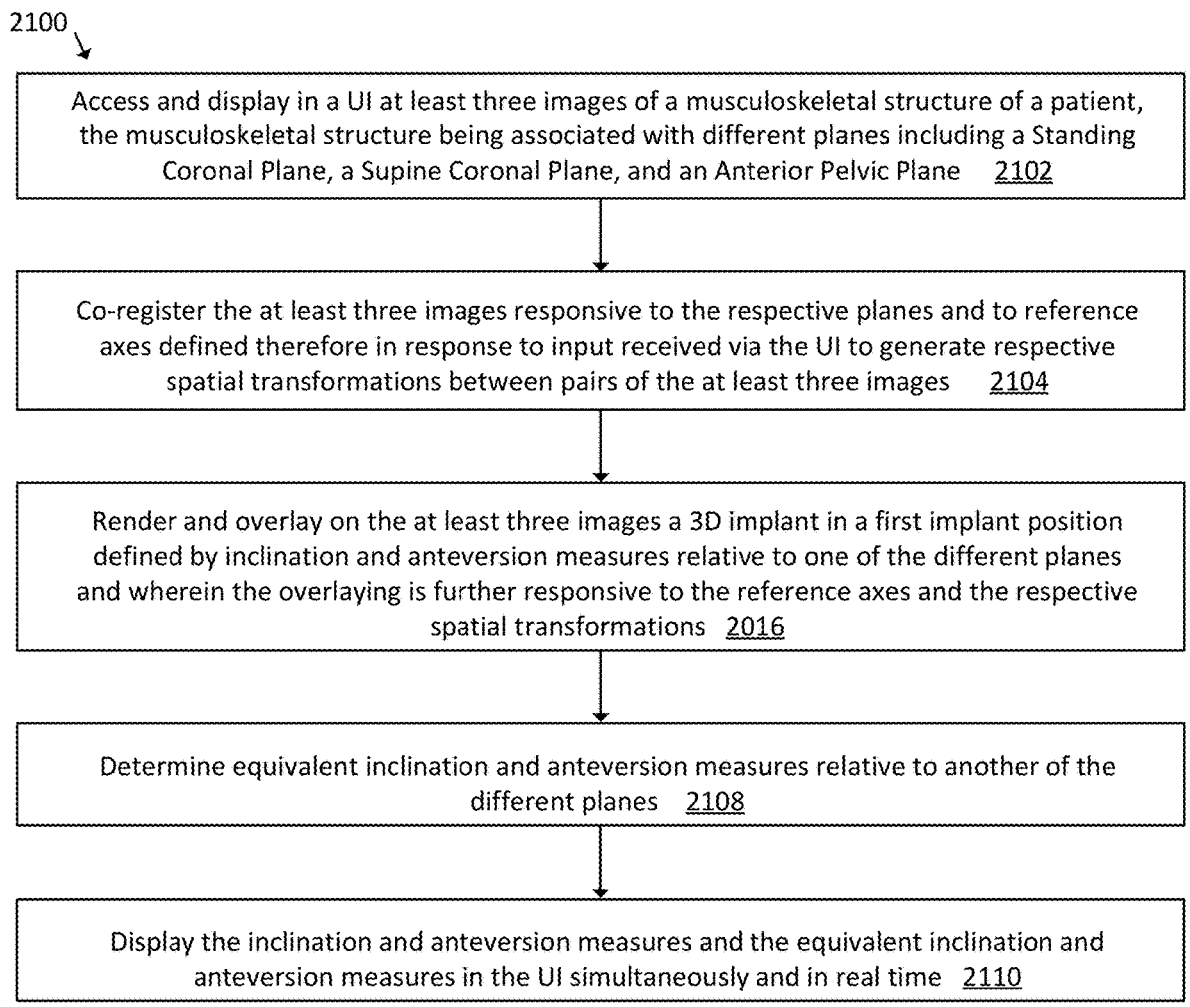

FIG. 21 is a flowchart of operations 2100 for a computing device such as computing device 900. Operations may provide a method to simultaneously display at least three images of musculoskeletal structure associated with different planes, for example, a Standing Coronal Plane, a Supine Coronal Plane, and an Anterior Pelvic Plane.

At 2102 operations access and display in a UI at least three images of a musculoskeletal structure of a patient, the musculoskeletal structure being associated with different planes including a Standing Coronal Plane, a Supine Coronal Plane, and an Anterior Pelvic Plane. At 2104 operations co-register the at least three images responsive to the respective planes and to reference axes defined therefore in response to input received via the UI to generate respective spatial transformations between pairs of the at least three images. At 2106 operations render and overlay on the at least three images a 3D implant in a first implant position defined by inclination and anteversion measures relative to one of the different planes and wherein the overlaying is further responsive to the reference axes and the respective spatial transformations. At 2108 operations determine equivalent inclination and anteversion measures relative to another of the different planes. At 2110 operations display the inclination and anteversion measures and the equivalent inclination and anteversion measures in the UI simultaneously and in real time.

Operations 2100 of the computer implemented method may further comprise: receiving an input via the UI to move the 3D implant to a second implant position defined by inclination and anteversion measures relative to one of the different planes; rendering and overlaying the 3D implant in the at least three images in accordance with the second implant position, the overlaying further responsive to the reference axes and the respective spatial transformations; determining equivalent inclination and anteversion measures for the second implant position relative to another of the different planes; and displaying the inclination and anteversion measures and the equivalent inclination and anteversion measures for the second implant position in the UI simultaneously and in real time.

Figure 22:
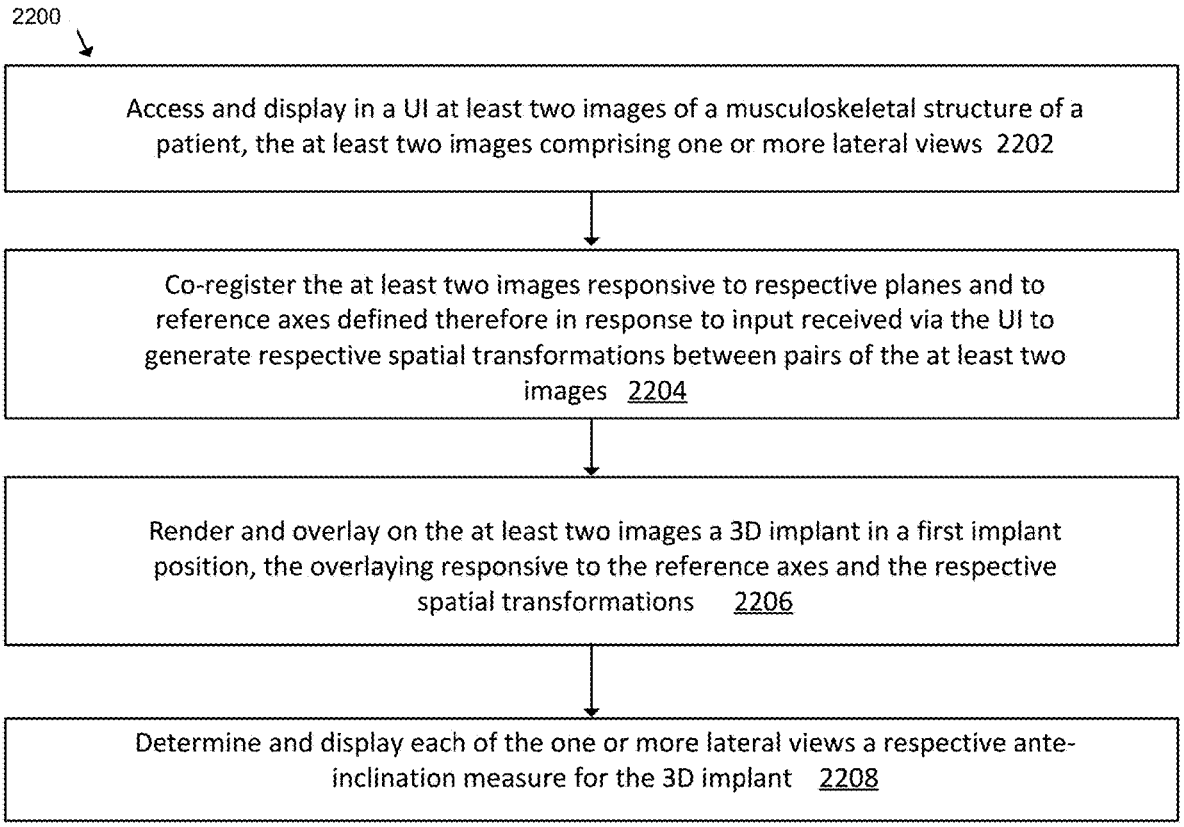

FIG. 22 is a flowchart of operations 2200 for a computing device such as computing device 900. Operations 2200 provide a computer implement method to determine (and optionally display) an ante-inclination measure.

At 2200 operations access and display in a UI at least two images of a musculoskeletal structure of a patient, the at least two images comprising one or more lateral views. At 2204 operations co-register the at least two images responsive to respective planes and to reference axes defined therefore in response to input received via the UI to generate respective spatial transformations between pairs of the at least two images. At 2206 operations render and overlay on the at least two images a 3D implant in a first implant position, the overlaying responsive to the reference axes and the respective spatial transformations. At 2208 operations determine and display each of the one or more lateral views a respective ante-inclination measure for the 3D implant.

Operations 2200 may further comprise: receiving an input via the UI to move the 3D implant to a second implant position; rendering and overlaying the 3D implant in the at least two images in accordance with the second implant position, the overlaying further responsive to the reference axes and the respective spatial transformations; and determining and displaying in each of the one or more lateral views a respective ante-inclination measure for the second implant position.

Computer Tablet Integration

Figure 23:
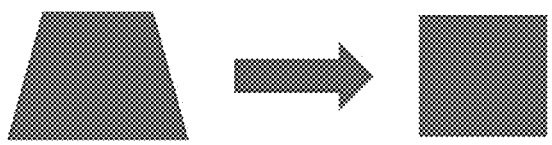
FIG. 23 is a block diagram representing skew error and a transformation to correct skew error.

Any of the computer methods herein may be configured to work through a web browser on a tablet. The required imaging can be uploaded to the tablet such as by using a camera on the tablet. A picture of a screen displaying the respective radiographic images may be taken and identified. Since it is difficult to ensure that the tablet is perfectly positioned, it is possible to correct for rotation and skew error as shown in FIG. 23.

One method of accomplishing this correction involves the identification of the four image corners, either through manual selection, through automatic image processing algorithms, or a combination of both, and calculating a transformation which causes these corners to be square with the edges of the image parallel to the edges of the display, applying this transformation to some or all points on the image. A person of ordinary skill will be aware of unwarping and similar such techniques.

Safe Zone Visualization

As briefly described herein above, surgeons often reference a so-called "safe zone" of the cup. This refers to a region (defining a 3D space) of cup angles which could be a factor in reducing post-operative dislocations. The safe zone is generally described by an inclination/anteversion pair of angles, and a range of acceptable deviation. One such safe zone might be 40/20 degrees radiographic inclination/anteversion and ±10 degrees of range. In accordance with the teachings of various practitioners, etc., different safe zones and/or ranges may be proposed.

Figure 24:
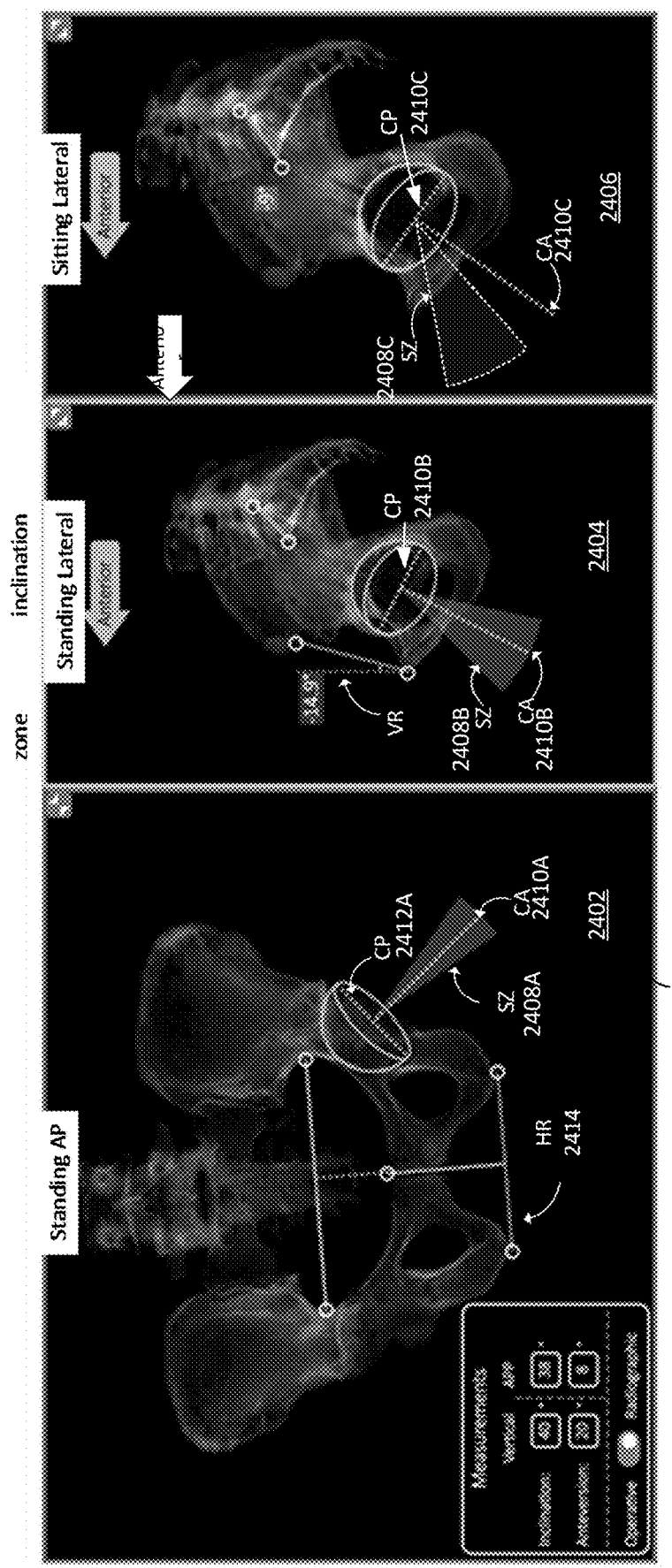
FIGS. 24-26 are illustrations of a portion of a GUI showing four respective images enabled to receive input of coordinates and determine (e.g. compute) clinically relevant values therefrom, and to display a safe zone indicator.
Figure 25:
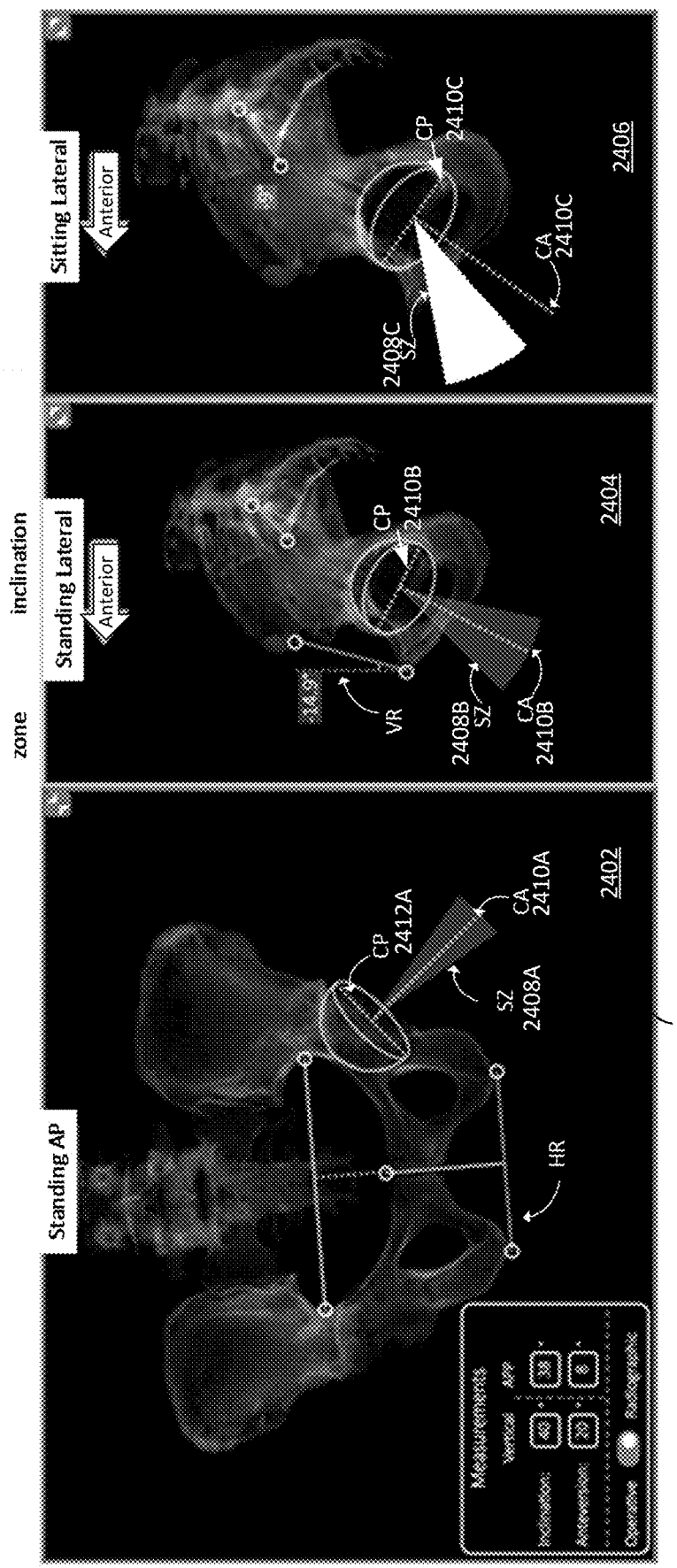
Figure 26:
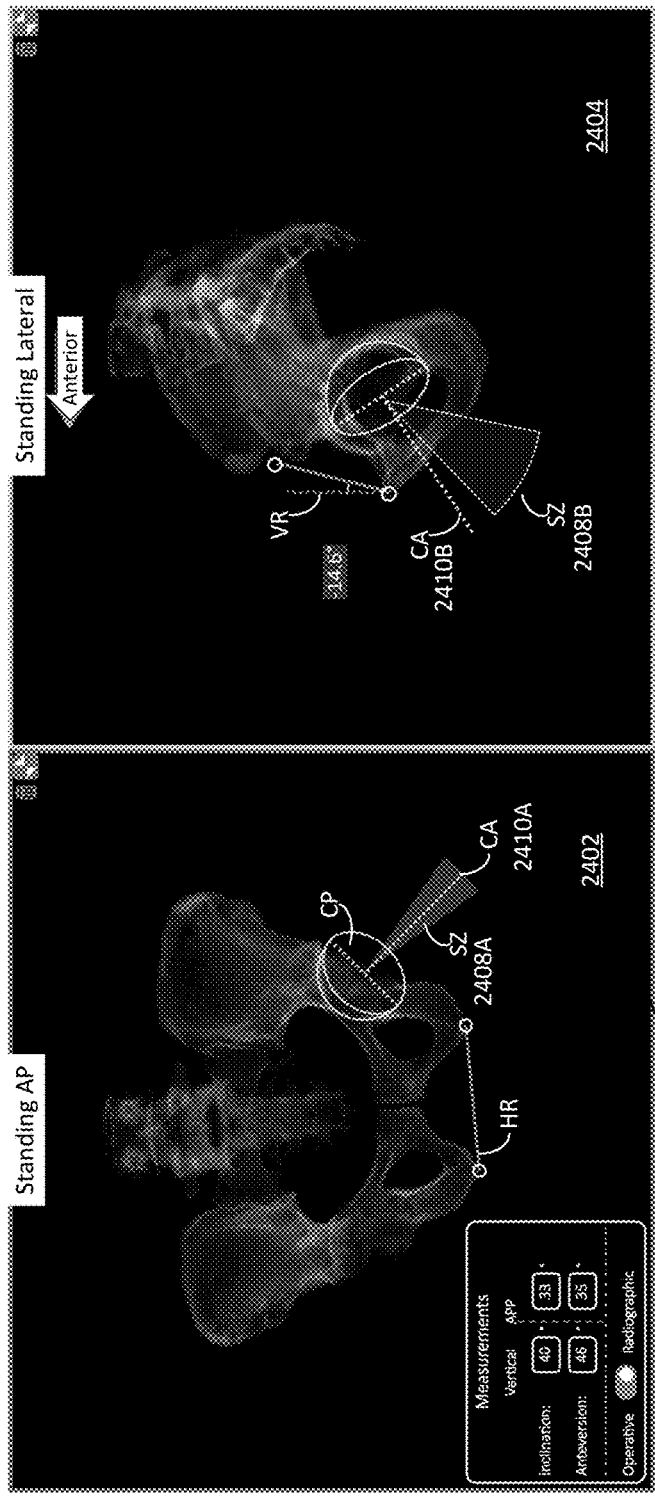
Figure 27B:
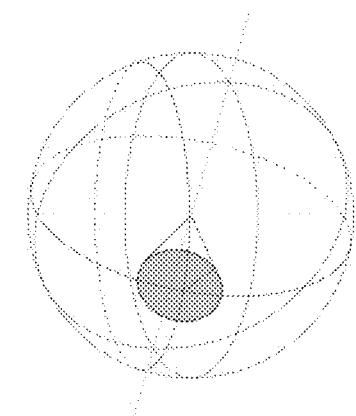
FIGS. 27A and 27B are illustrations showing a safe zone defined as a 3D sector of a sphere (e.g. defined relative to the angles and ranges of inclination and anteversion.
Figure 27A:
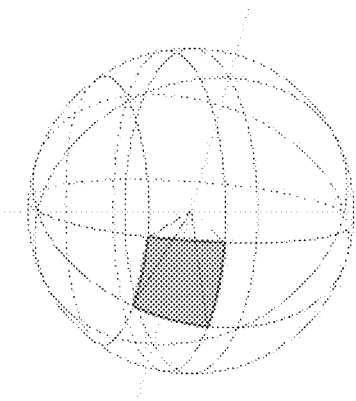

A computer implemented method may provide a visualization such as a safe zone graphical element rendered and overlaid for one safe zone or more than one safe zone. FIGS. 24-26 are illustrations of a portion of a GUI 2400 showing a save zone visualization over images 2402, 2404 and 2406. FIG. 26 shows only images 2402 and 2404. In FIGS. 24-26, the safe zone (SZ) 2408A, 2408B and 2408C is visualized by a safe zone graphical element in the form of an arc which may be colored on a display screen, with a dotted line (e.g. a central cup axis (CA) 2410A, 2410B and 2410C) perpendicular to the cup face indicating the position of the cup is inside or outside this arc. Color is not shown in the drawings as filed. A dotted line CP 2412A, 2412B and 2412C may also illustrate the cup plane across the cup face. In FIG. 24, GUI 2400 shows Standing AP/Standing Lateral cups are in the safe zone and Sitting Lateral cup is outside of the safe zone. FIG. 25 shows SZ 2408C as opaque when the sitting lateral cup is outside the safe zone.

The safe zone graphical element may be differently displayed in each of the images. For each of the images the respective safe zone graphical element may have respective graphical characteristics. At least one of these characteristics is selected according to whether (relative to a particular image) the 3D implant is in the safe zone in the particular image. For example, a characteristic may be color. A color of the arc may be used to indicate when the cup is within the safe zone (for example, green for inside, red for outside of the safe zone). In FIG. 24, the safe zone of the Sitting Lateral view (relative to images 2406) is red when viewed in color and highlighted with a dotted white outline for emphasis to show the cup is outside (without) the safe zone SZ 2408C. Other visualization features (graphical characteristics) of the safe zone may be used such as a change of state (blinking or light intensity, color changing) to distinguish the safe zone arc or the border thereof from inside to outside indicating.

A different overlay style may be used to distinguish in from out. A different overlay style may be used such as using at least partially transparent color for the arc when the 3D implant is inside and using opaque when it is outside (e.g. FIG. 25 Sitting Lateral view (rightmost)), or from a using consistent transparency to alternating transparent/opaque stripes or sections (e.g. warning bars, checkered flag (not shown)), etc.

Alternatively or in addition, an audible signal or haptic feedback (e.g. device vibration) may be provided via output devices. Alternatively or in addition, the visualization of the line normal to the cup face may be varied to indicate whether the cup is within or without of the safe zone (e.g. color, blinking, dotted vs. solid, etc. (not shown)).

The computer method may render and overlay a 3D implant respectively for each of the at least two images in a first position relative to reference axes, and according to each respective spatial transformation; and render and overlay respectively for each of the three images a safe zone graphical element indicating a clinically accepted safe range of positions for the 3D implant.

The safe zone graphical element may be a respective graphical element for each of the images. Each respective graphical element may have respective graphical characteristics, for a particular image of the images, the respective graphical characteristics are selected based on a determination whether the 3D implant is positioned inside or outside the clinically accepted safe range of positions in the particular image.

As a planning position of the cup is adjusted (e.g. using object handles in a GUI, or through the measurement input fields), the color and/or other visual features of the safe zone and/or cup axis line CA may change and other feedback signals provided based on the angles of the cup. This gives the user intuitive visual (and/or auditory, etc.) feedback on the cup location, rather than thinking about numbers and ranges. Thus, the computer method may receive input representing a second position of the 3D implant; render and overlay accordingly the 3D implant in the second position to update, in at least near real time, each of the at least two images respectively; determine for each particular image, whether the second position is inside or outside the clinically accepted safe range of positions in the particular image; select the respective graphical characteristics accordingly; and render and overlay the respective graphical element for each of the images.

The safe zone here is calculated relative to the horizontal reference (HR) 2414 line shown in purple in FIG. 24-26 when viewed in color) on the standing AP image (leftmost), and relative to the coronal plane of the pelvis (line VR for the vertical axis of the standing lateral image (middle)). In the computer method, the clinically accepted safe range of positions may defined in accordance with at least two angles relative to the reference axes and an associated range of position for each angle.

The safe zone can be imagined as a 3D sector of a sphere (e.g. defined relative to the angles and ranges of inclination and anteversion). This sector may be defined as a rectangular pyramidal sector shown in FIG. 27A, where the sector is defined with two pairs of angles, start and end, from the horizontal equator of the sphere, and from a vertical reference line. The sector may be defined as a conical sector, where there is a pair of angles, relative to vertical and horizontal references on the sphere, and a radial distance away from this indicated set of angles, shown in FIG. 27B.

The visualizations of that sector can be rendered in a desired style or format as the projections on to the 2D views. As noted, three such views are shown in FIGS. 24 and 25 and two in FIG. 26. A determination may be made whether the 3D implant is inside or outside the safe zone to determine the appropriate style or format (graphical characteristics) of the safe zone graphical element and/or axis line CA to render and display. The dotted line from the cup, representing an axis normal to the cup face, is present within or without the respective sector in each particular 2D view as a visual aid. The computer implemented method may render and overlay an axis line extending from the 3D implant to assist with visualizing the 3D implant relative to the clinically accepted safe range of positions.

Particular safe zones (i.e. 3D sectors) could be defined by respective clinically relevant research (e.g. Lewinnek et al.; etc. as noted above), or could be defined individually by the surgeon. A button or other GUI interface (not shown) may be provided to select a desired safe zone sector determined by the respective research for visualization or to permit definition of a zone by the surgeon or other user. Alternatively or in addition (not shown) more than one of the safe zones may be visualized (e.g. showing safe zones from two clinically relevant research sources). Any overlap in the e.g. two zones ay be visualized by a third color (e.g. a first safe zone visualized in yellow, a second safe zone visualized in blue and any overlap visualized in green (e.g. via additive coloring)). Thus in the computer implemented method the clinically accepted safe range of positions is predefined in accordance with a defined standard or selectively defined in accordance with input received. The computer implemented method may comprise receiving input to select between the clinically accepted safe range of positions as predefined in accordance with the defined standard or as selectively defined in accordance with input received.

FIG. 28 is a flowchart of operations 2800 of a computing device such as a computing device 900. The operations may provide a computer implemented method to visualize a safe zone relative to an implant in multiple images.

At 2802 operations access and display at least two images of a musculoskeletal structure of a patient, where one pair of images are of different views of a first position or are of a same view in different functional positions. At 2804 operations define reference axes of the musculoskeletal structure on at least one of the at least two images, based on user input.

At 2806 operations determine a spatial transformation between the at least two images based on the reference axes. At 2808 operations determine a positional change parameter of the musculoskeletal structure if one pair of the at least two images is the same view in different functional positions, the positional change parameter representing the positional change of the patient between the different functional positions. At 2810 operations render and overlay a 3D implant respectively for each of the images in a first position relative to the reference axes and according to the spatial transformation and the positional change parameter, if applicable. At 2812 operations render and overlay respectively for each of the three images a safe zone graphical element indicating a clinically accepted safe range of positions for the 3D implant.

A computer implemented method may provide a centering feature whereby for a particular safe zone, a button or other GUI interface (not shown) may be invoked to automatically position the cup such that the cup axis is in the center of the safe zone, as much as possible in each of the 2D views. A "best fit" may be made. The problem could be stated as a combined minimization in multiple views, and solved using linear or non-linear optimization.

If it is not possible to center (or otherwise locate) the cup position in each safe zone, there may be provided fixed rules to govern where the default cup position is defined and/or a control to provide user adjustment to a desired position. Thus the computer implemented method may comprise: receiving via a control interface an input to automatically locate the 3D implant within the clinically accepted safe range of positions relative to each of the images; positioning the 3D implant in a safe zone position responsive to the clinically accepted safe range of positions in each of the images; and rendering and overlaying the 3D implant in the safe zone position in each of the images. It may further be that positioning the 3D implant comprises determining a best fit for the safe zone position relative to each of the images. The computer implemented method may, for each respective image of the images, update a rendering and overlaying of the safe zone graphical element responsive to whether the safe zone position of the 3D implant is inside or outside the clinically accepted safe range of positions. The safe zone visualization may be performed along with the other methods described herein.

Thus there is provided a computer implemented method (for safe zone visualization) comprising: accessing and displaying at least two images of a musculoskeletal structure of a patient, where one pair of images are of different views of a first position or are of a same view in different functional positions; defining reference axes of the musculoskeletal structure on at least one of the at least two images, based on user input; determining a spatial transformation between the at least two images based on the reference axes; determining a positional change parameter of the musculoskeletal structure if one pair of the at least two images is the same view in different functional positions, the positional change parameter representing the positional change of the patient between the different functional positions; rendering and overlaying a 3D implant respectively for each of the images in a first position relative to the reference axes and according to the spatial transformation and the positional change parameter, if applicable; and rendering and overlaying respectively for each of the three images a safe zone graphical element indicating a clinically accepted safe range of positions for the 3D implant.

The safe zone graphical element may comprise a respective graphical element for each of the images, each respective graphical element having respective graphical characteristics and wherein, for a particular image of the images, at least one of the respective graphical characteristics is selected based on a determination whether the 3D implant is positioned inside or outside the clinically accepted safe range of positions in the particular image. The respective graphical characteristics may comprise color, pattern, transparency, shape outline and change of state comprising blinking (intensity level) and color change. The computer implemented method may comprise: receiving input representing a second position of the 3D implant; rendering and overlaying accordingly the 3D implant in the second position to update, in at least near real time, each of the images respectively; determining for each particular image, whether the second position is inside or outside the clinically accepted safe range of positions in the particular image; and selecting the respective graphical characteristics accordingly and rendering and overlaying the respective graphical element for each of the images.

The computer implemented method may further comprising providing auditory and/or haptic feedback responsive to the determining when the second position is outside clinically accepted safe range of positions.

In the computer implemented method, rendering and overlaying the 3D implant may include rendering and overlaying an axis line extending from the 3D implant to assist with visualizing the 3D implant relative to the clinically accepted safe range of positions.

In the computer implemented method the clinically accepted safe range of positions may be defined in accordance with at least two angles relative to the reference axes and an associated range of position for each of the at least two angles. The 3D implant may be an acetabular cup and the at least two angles are an inclination angle and an anteversion angle.

In the computer implemented method the clinically accepted safe range of positions may be predefined in accordance with a defined standard or selectively defined in accordance with input received. The computer implemented method may further comprising receiving input to select between the clinically accepted safe range of positions as predefined in accordance with the defined standard or as selectively defined in accordance with input received.

The computer implemented method may comprise: receiving via a control interface an input to automatically locate the 3D implant within the clinically accepted safe range of positions relative to each of the at least two images; positioning the 3D implant in a safe zone position responsive to the clinically accepted safe range of positions in each of the at least two images; and rendering and overlaying the 3D implant in the safe zone position in each of the at least two images. In the computer implemented method, positioning the 3D implant may comprise determining a best fit for the safe zone position relative to each of the at least two images. The computer implemented method may comprise, for each respective image of the at least two images, updating a rendering and overlaying of the safe zone graphical element responsive to whether the safe zone position of the 3D implant is inside or outside the clinically accepted safe range of positions.

In the computer implemented method the at least two images may be three images; wherein one pair of the three images being of different views of a first position, and another pair of the three images being of a same view in different functional positions; and wherein the method comprises determining a positional change parameter of the musculoskeletal structure based on the other pair showing the same view in different functional positions, the positional change parameter representing the positional change of the patient between the different functional positions; and wherein determining the spatial transformation between the other pair utilizes the positional change parameter.

A computing system may be configured to perform the computer implemented method for safe zone visualization and safe zone visualization may be combined with other features and functions described herein.

Revision Surgery

The following subject matter relates to revision surgery where an existing (first) implant is replaced with a new (second) implant.

During Revision THA, the surgeon is replacing an existing hip implant comprising a cup with a new hip implant. In the case where the cup is stable (but is being replaced due to wear, or incorrect positioning), the orientation of the cup can be measured relative to known anatomic planes (e.g. the APP, or the supine coronal plane for example).

Figure 29:
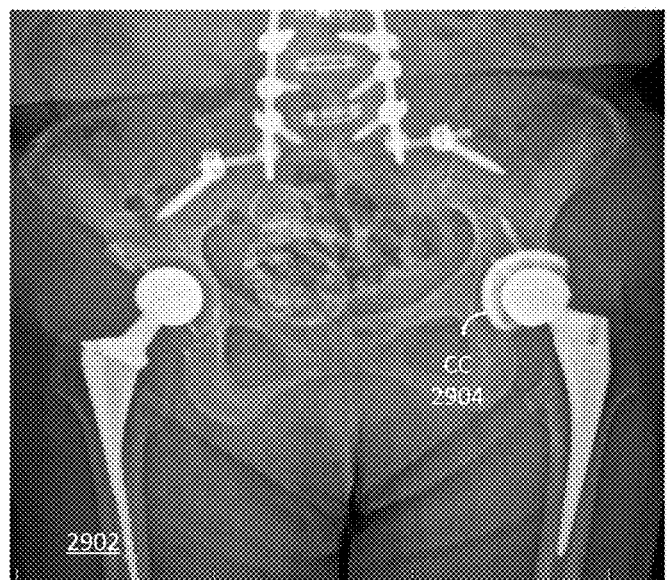
FIGS. 29-31 are illustrations of a portion of a GUI 2900 showing an image 2902 of post-operative anatomy.
Figure 30:
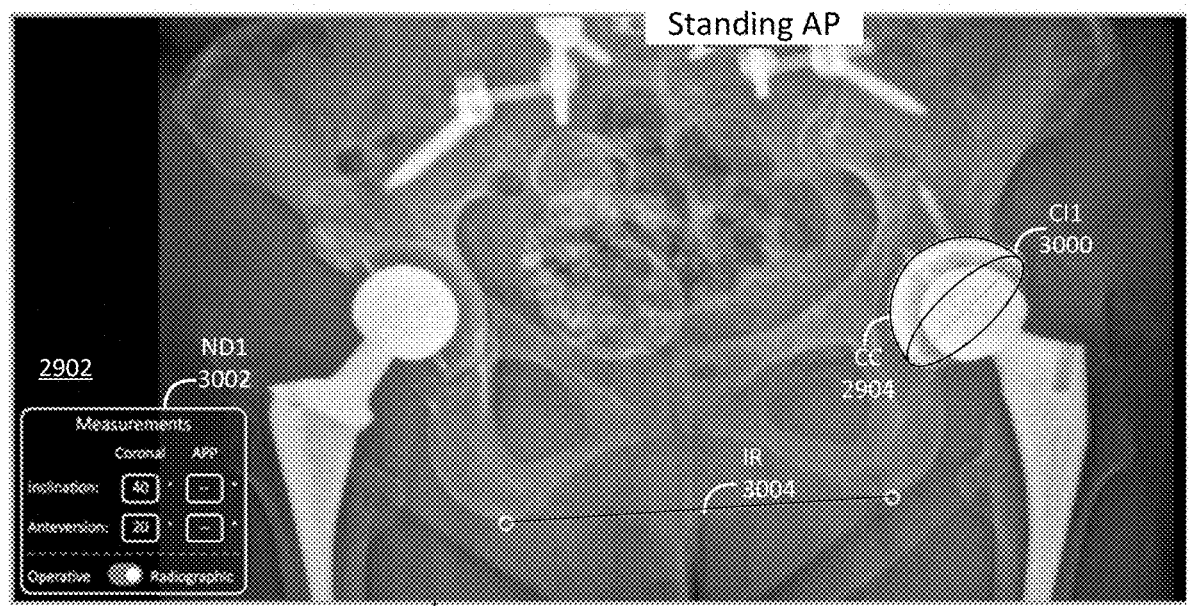
Figure 31:
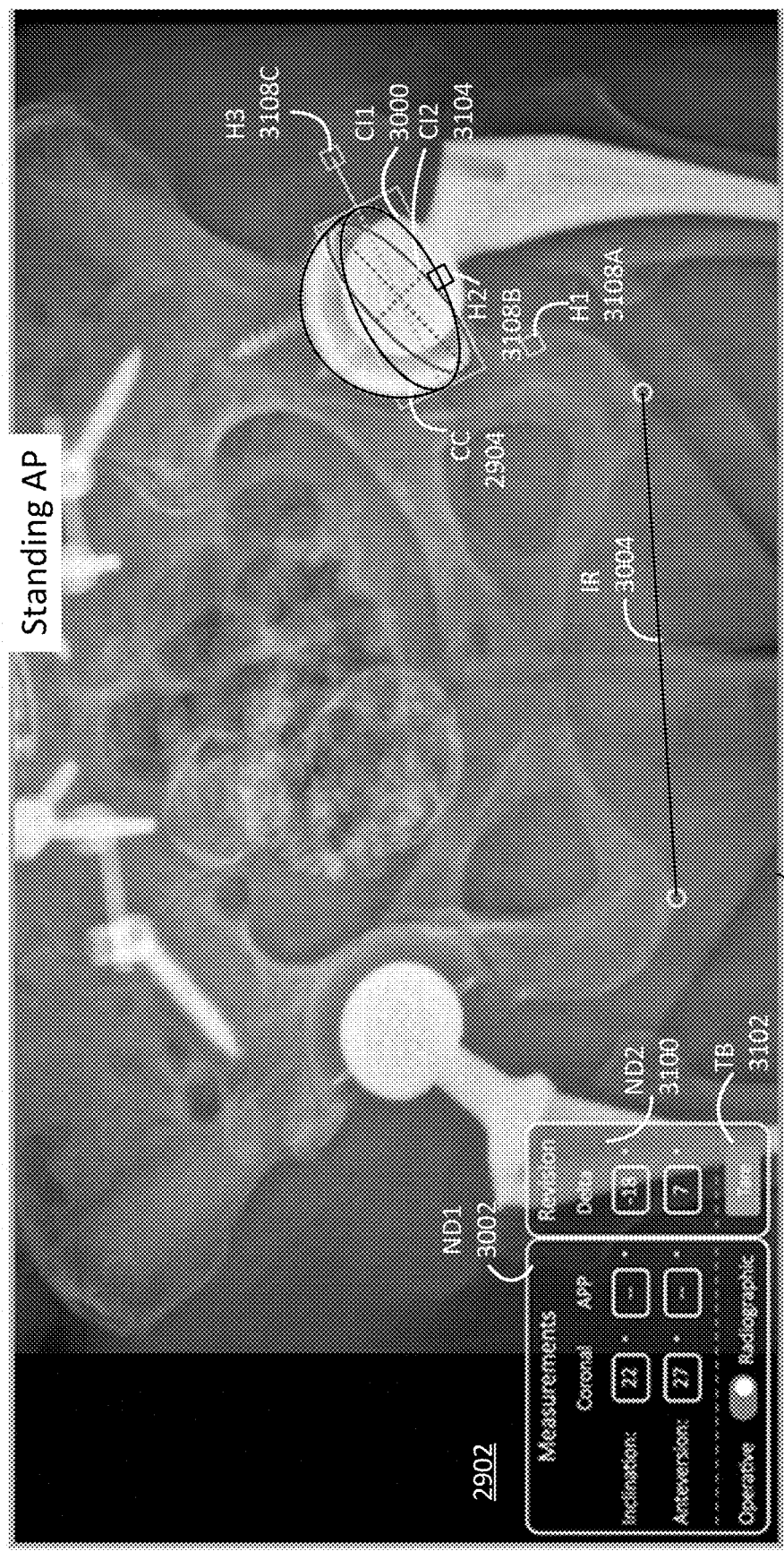
Figure 32:
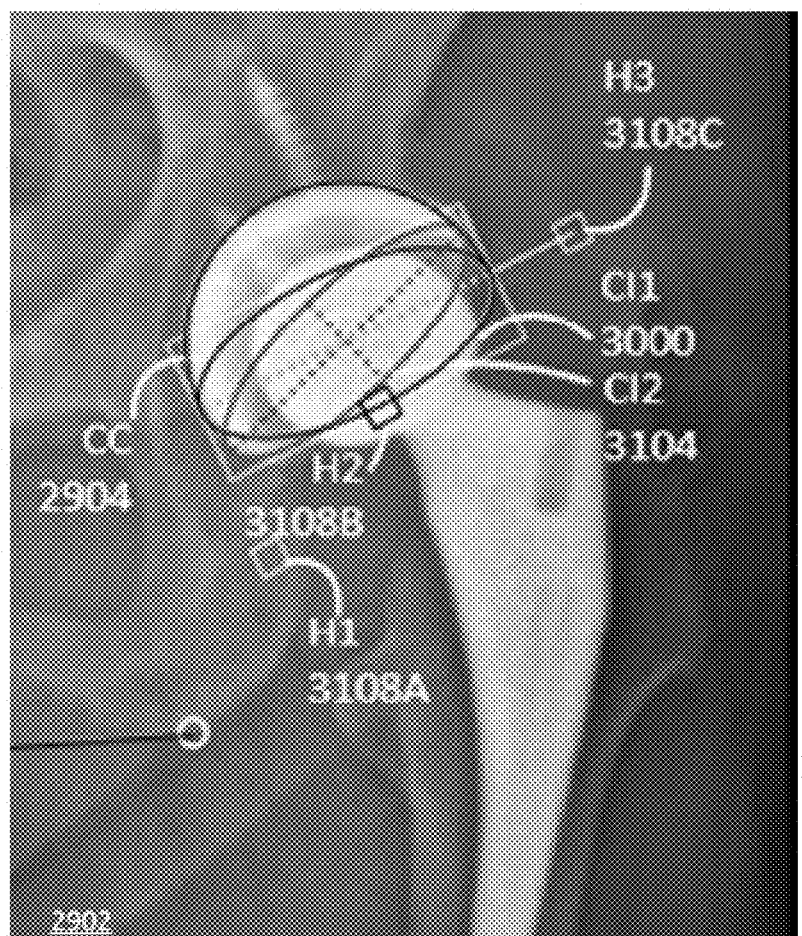
FIG. 32 is an enlarged view of a portion of the GUI of FIG. 31.
Figure 33A:
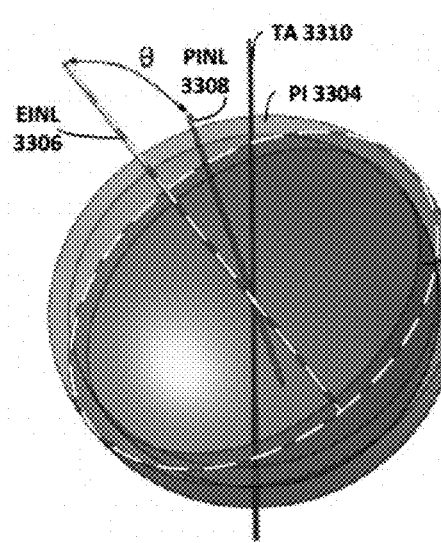
FIGS. 33A and 33B are illustrations of cup implants as hemispheres to show calculations of inclination and anteversion delta measurements.
Figure 33B:
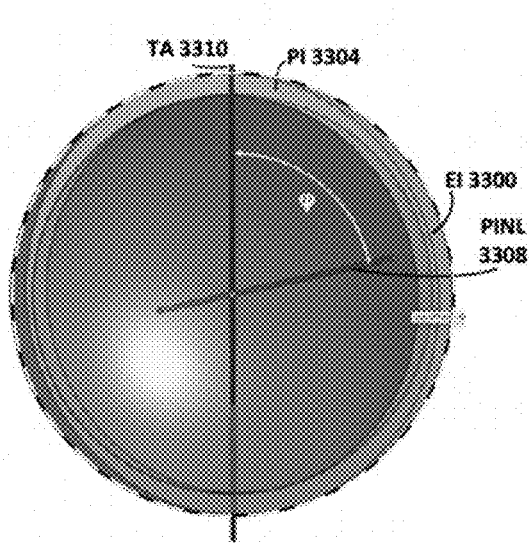

FIGS. 29-31 are illustrations of a portion of a GUI 2900 showing an image 2902 of post-operative anatomy. FIG. 32 is an enlarged view of a portion of FIG. 31. GUI 2900 may be configured as the other GUIs are, namely, with the ability to receive input, define reference axes, co-register images, define other measurements, show various overlays, etc. GUIs may present one or more images.

According to a computer implemented method, during the pre-op planning stage, a pre-op image (e.g. x-ray or other modality) may be obtained by the computer and displayed via a display device as shown in FIG. 29. FIG. 29 shows the current cup (CC) 2904 in a left hip as viewed from the posterior of the patient in an x-ray image.

The computer implemented method may render and overlay a 3D implant, and display numerically the position of the 3D implant such as in terms of angles (e.g. inclination and anteversion) from defined anatomical axes or planes (e.g. coronal, APP). FIG. 30 shows image 2902 comprising a standing AP x-ray with various GUI elements overlaid thereon.

One overlay is a 3D implant (a first cup implant CI1 3000). By overlaying the 3D implant CI1 3000 in alignment with the corresponding implant structure of the patient in the image (e.g. current cup CC 2904 in the Standing AP x-ray), the position of the corresponding implant structure (current cup CC 2904) relative to an axis may be determined from the position of the 3D implant. The measurement may be displayed such as in a GUI element for a numerical display (ND1 3002). A graphical user interface may be configured to provide object handles for the 3D implant overlay with which to move the 3D implant (overlay) CI1 3000 and align it with the corresponding implant structure or otherwise move it. In FIG. 30, when viewed in color, the 3D implant CI1 is blue and shows the visual position (over the current cup CC 2904 in the radiograph). The measurements in ND1 3002 show the angles (i.e. a current position) of the 3D implant CI1 3000. When overlaid on the cup CC 2904 these numbers represent the measurement of the corresponding implant structure in the patient. An inclination reference 3004 (IR) (e.g. axis for the image) may be established (e.g. inputs received to determine end points) and displayed.

Measuring the inclination and anteversion may be performed according to one or more methods. For example, a computer implemented method may provide a 3D implant object with handles (as shown elsewhere herein) and as shown in FIG. 31 for a user to manually fit (e.g. position and size) the 3D implant appropriately over the current cup CC in one image or two or more co-registered images. Two of the co-registered images made of the same functional position from different views (e.g. standing AP and standing lateral views). Controls to zoom in or zoom out the display, to enlarge or shrink image size and 3D implant size, may assist with appropriate resolution to permit a user to fit the 3D implant. In a more automatic fashion, for example, a computer implemented method may automatically fit a 3D implant object to a current cup CC such as by using image processing to determine the location of the current cup CC in one image or two or more co-registered images. It may use edge detection and determine a cup face and the applicable pose as defined relative to inclination and anteversion. Automatic and manual methods may be combined or provided as options. A 3D implant may be automatically fit and a user permitted to manually adjust the fit.

The computer implemented method may provide a control (e.g. a button, a menu item, a voice activated control) to receive input to invoke a revision tool. The GUI may be configured to display an additional graphical element for numerical display (e.g. ND2 3100) such as shown in FIG. 31. The additional graphical element may be a second numerical display to show a second set of measurements as described further. The GUI may also show a "Tare" button (TB) 3102 (or other control interface) to receive input to establish a reference cup position (similar to taring a scale). When the tare button is invoked, the current position (absolute angles 40° inclination and 20° anteversion) of the 3D implant CI1 3000 is stored. Visually, a further graphical element representing the 3D implant (e.g. a second 3D implant overlay CI2 3104) may be displayed and maintained in the reference cup position. When viewed in color the overly CI2 3104 may be maroon in color. Though not shown, a control may be provided to turn the display of CI2 3104 on or off. CI2 may be distinguished from CI1 in the GUI such as by a difference of color, line style, shape or other appearance characteristics.

The position of the first 3D implant overlay CI1 3000 may be moved to a second position such as via one or more handles (H1 3108A, H2 3108B and H3 3108C) or via input to the numerical display ND1 3002 to adjust one or both of the angles. Input to adjust angles (measurement data) may invoke the GUI to update the position of CI1 3000 (to render and overlay it in a second position) in the display over the patient image 2902 to accord with the input. Input to the numerical display may comprise receiving a specific angle number (e.g. 22) or a control input to raise or lower the present number (e.g. to add or subtract 1° via a respective plus/minus or other control (not shown)). The computer implemented method may update the displaying of the current position (e.g. in ND1 3002) in response to a movement of the 3D implant (e.g. via the handles) such as in real time.

FIG. 31 shows CI1 3000 in a second position where the cup inclination has decreased by 18 degrees, and the cup anteversion has increased by 7 degrees. The numerical display elements ND1 3002 and ND2 3100 may present the absolute angle references (ND1 3000) of CI1 3000 and the change or delta measurement) in such measurements for CI1 3000 relative to the reference cup position previously saved using the tare button TB. Thus the computer implemented method may determine and store a delta measurement comprising a difference between the reference position and the second position and display this delta measurement.

As shown in FIG. 31, GUI 2900 provides both a visual indication of the change in cup position by showing two overlays (with CI2 3104 in the reference position (maroon) vs CI1 3000 in the second position (cyan)), and the cup orientation numbers in a relevant coordinate system.

The output of the planning session for a revision surgery (as provided by the computer implemented method) is now a "delta" target, instead of an absolute cup position target. Such data may be saved to a memory (or other storage device) and/or communicated to another computer apparatus, etc. for use during a surgical procedure such as one involving an intraoperative surgical navigation or localization system. In one example, the data may be encoded such as in a matrix barcode (e.g. a Quick Response (QR) code— QR Code is a registered trademark in the United States of Denso Wave Incorporated) and communicated such as via a display device or printout.

This target may be communicated to an intraoperative surgical navigation system which has the ability to measure relevant anatomic landmarks (such as coronal plane, APP, etc.) to be used for anatomic reference axes, and has the ability to measure the position of an existing implant relative to this registration. When the reference axes of the surgical navigation system are the same as the reference axes of the planning software, and the subject of the measurement (i.e. the patient) is the same, the communicated target can be received by the surgical navigation system and, in conjunction with the intra-operative measurement, provide an intraoperative target which minimizes error due to discrepancies in the reference axes, such discrepancies possibly arising from factors such as soft tissue, mis-probing, incorrect patient positioning, etc.

Since absolute measurements in a respective intraoperative surgical navigation or localization system and method to assist with surgery and a respective surgical planning computer system and method are made relative to their respective coordinate systems, such coordinate systems must be aligned for the absolute measurements to be related. However, by determining and utilizing a change in absolute measurements (i.e. "delta" measurements in both the planning and intraoperative surgical systems), the differences in the two coordinate systems may be negated. The relationship between the "delta" measurements in a planning system and method and the "delta" measurements in the intraoperative system and method are less affected by discrepancies between the coordinate systems of the respective applications.

The "delta" target has been described above as being communicated in an anatomically relevant coordinate system, e.g. radiographic inclination/anteversion relative to the standing coronal plane. By relying on a "delta" instead of absolute measurements, small discrepancies in reference axes between planning software and surgical navigation software can have minimal impact on final implant positioning. The target could instead by described and communicated in a reference coordinate system relative to the existing implant itself, or relative to a combination of the implant and anatomic measurements. This could reduce any discrepancies between reference axes in the respective planning and navigation software due to the fact that implants are more accurately measured in both software/systems than are anatomical landmarks.

In one example, a "delta" target for an acetabular implant (represented as a hemisphere), could be described with two angles of change: a theta angle which represents the angle between the existing and target cup normal vectors, and a phi angle representing the rotation of this change relative to the transverse axis of the patient. Normal vectors are relative to the face of each respective implant. FIG. 32A represents cup hemispheres 3200 and 3202 for the existing implant and a planned implant respectively. In FIG. 32A, the existing implant is represented as the hemisphere EI 3200 (having a broken line on the outer margin of the cup face) with a normal line EINL 3206 (also shown broken in style), and the planned implant 3202 is represented as the hemisphere PI 3202 with a normal line PINL 3208. FIG. 32A shows how theta ($\theta$) is the absolute angle between the normal of the planned implant PINL 3208 and the normal of the existing cup EINL 3206.

FIG. 32B shows the same cups as hemispheres 3200 and 3204 from a position perpendicular to the existing cup face (the existing cup normal vector EINL 3206 points towards reader) and phi ($\varphi$) is the angle between the red transverse axis TA 3210 of the body, and the planned cup vector PINL 3208, when both are projected onto the face of the cup. The computer implemented method may be configured to generate the delta measurements relative to the existing implant. With reference to the FIG. 30 and FIG. 31, a 3D implant CI1 3000 is overlaid on the current cup 2904 (existing implant). A reference position is established such as by invoking the Tare control 3102. A second 3D implant CI2 3104 is overlaid to mark the reference position. The 3D implant overlay CI1 3000 is moved to the planned input position (see FIG. 31). Values theta and phi may be determined between the reference position and the planned position, for example, using the model of the 3D implant (to determine the plane of the cup face and any normal thereto) and its two locations in the coordinate system of the radiographic system. Determining these two angles determines the changes for the planned implant relative to the existing implant without requiring an association with the coordinate system of the radiographic image.

Though only one radiographic image is shown in FIGS. 30 and 31, two co-registered views (or more) may be shown such as illustrated elsewhere herein. Movement of CI1 3000 in a particular view (e.g. such as by manual adjustment via handles, etc.) may be reflected in the other view(s) accordingly such as described elsewhere herein. A suitable spatial transformation (more than one) may be determined for appropriately rendering and overlaying the 3D implant and any save original position as represented by CI2 3104.

Figure 34:
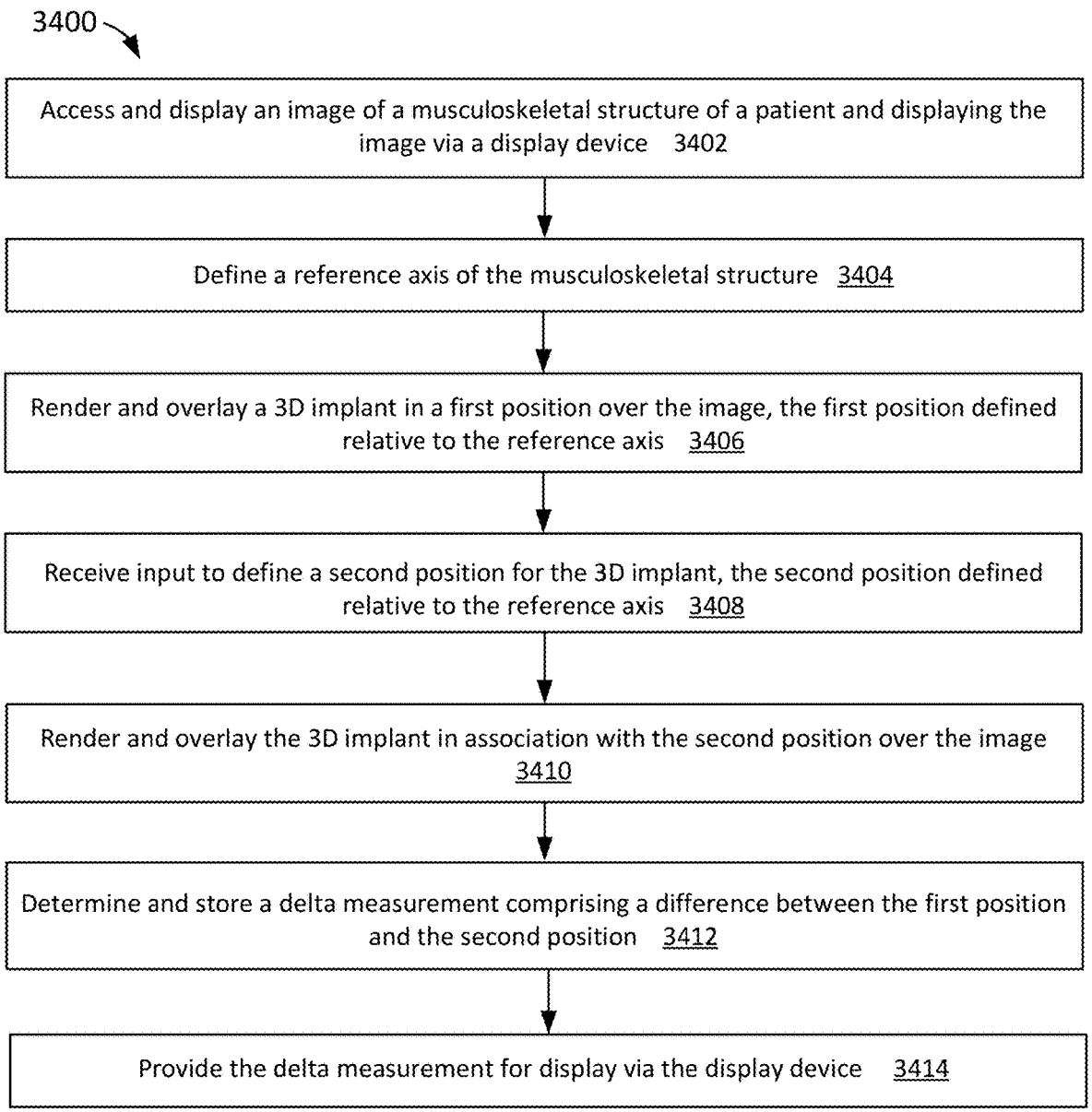
FIG. 34 is a flowchart of operations of a computing device in accordance with the teachings herein.

FIG. 34 is a flowchart of operations 3400 for a computing device such as the computing device 900. Operations 3400 may provide a method for preoperative planning for revision surgery.

At 3402 operations access and display an image of a musculoskeletal structure of a patient and displaying the image via a display device. At 3404 operations define a reference axis of the musculoskeletal structure (e.g. from input received or as received from previous computation).

At 3406 operations render and overlay a 3D implant in a first position over the image, the first position defined relative to the reference axis. At 3408 operations receive input to define a second position for the 3D implant, the second position defined relative to the reference axis. At 3410 operations render and overlay the 3D implant in association with the second position over the image. At 3412 operations determine and store a delta measurement comprising a difference between the first position and the second position; and at 3414 operations provide the delta measurement for display via the display device.

Thus, there is provided a computer implemented method (e.g. for planning a revision surgery) comprising: accessing an image of a musculoskeletal structure of a patient and displaying the image via a display device; defining a reference axis of the musculoskeletal structure; rendering and overlaying a 3D implant in a first position over the image, the first position defined relative to the reference axis; receiving input to define a second position for the 3D implant, the second position defined relative to the reference axis; rendering and overlaying the 3D implant in association with the second position over the image; determining and storing a delta measurement comprising a difference between the first position and the second position; and providing the delta measurement for display via the display device.

The computer implemented may comprise receiving input to store the first position as a reference position for the 3D implant in a storage device. The computer implemented method may comprise rendering and overlaying a further graphical element representing the 3D implant in the reference position to distinguish the 3D implant as overlaid in the second position.

In the computer implemented method the 3D implant may be overlaid in alignment with a corresponding implant structure of the patient in the image and wherein the first position provides a measurement of the corresponding implant structure relative to the reference axis.

The computer implemented method may comprise displaying, via the display device, a current position of the 3D implant relative to the reference axis. The computer implemented may comprise updating the displaying of the current position in response to a movement of the 3D implant.

The computer implemented method may comprise providing a graphical user interface (GUI) to display handles for the 3D implant and to receive input to move the 3D implant over the image using the handles. The computer implemented method may comprise receiving input to define the first position via the handles for the 3D implant. The input may define a fit for the 3D implant over an implant in the patient visible in the image.

The computer implemented method may comprise fitting the 3D implant over an implant in the patient visible in the image using image processing.

The computer implemented method may comprise providing a GUI to receive measurement data relative to the reference axis and rendering and overlaying the 3D implant in accordance with the measurement data.

In the computer implemented method, the musculoskeletal structure may comprise a hip structure and the 3D implant comprises a cup implant.

In the computer implemented method the first position and the second position may be defined in accordance with an inclination angle and an anteversion angle.

The computer implemented method may be performed preoperatively using a computer apparatus configured to provide a preoperative planning system and wherein the method may comprise communicating the delta measurement to a computing apparatus configured to provide an intraoperative surgical system to facilitate a surgical procedure.

In the computer implemented, the image may comprise either: a preoperative image displayed preoperatively; or an intraoperative image displayed intraoperatively.

The computer implemented method may comprise determining the delta measurement as angles of change relative to an existing implant in the patient as represented by the 3D implant in the first position and the 3D implant in the second position.

The computer implemented method may comprise communicating the delta measurement for further processing. The further processing may be surgical navigation on the patient in the image using an intra-operative surgical navigation system, and the first position may be the same as a measured implant position for an implant in the patient as measured by the intra-operative surgical navigation system and the intra-operative surgical navigation system may be configured to measure a change to an implant position relative to the measured implant position.

In the computer implemented method the image may define a first image and the method may comprise: accessing a second image of the musculoskeletal structure of the patient and displaying the second image via the display device together with the first image; determining a spatial transformation between the first image and the second image; rendering and overlaying the 3D implant in the first position over the second image based on the reference axis and the spatial transformation to display the 3D implant respectively on both of the first image and the second image; and, in response to receiving input to define the second position, rendering and overlaying the 3D implant in association with the second position over the second image. The computer implemented method may comprise providing handles to interact with the 3D implant as overlaid on each of the first image and the second image and wherein the input to define the second position for the 3D implant comprises receiving input via the handles as provided on one of the first image and the second image. In the computer implemented method the first image and the second image may comprise different views of the same functional position.

Conclusion

The methods herein may be performed preoperatively or intraoperatively. That is, the image displayed may comprise either: a preoperative image (e.g. static x-ray or other image generated prior to an operation which is displayed preoperatively; or may be an image generated during a procedure ("an intraoperative image") that is displayed intraoperatively and the method to determine the delta measurements undertaken intraoperatively. Planning as described herein may include planning during a procedure, for example, in an operating room as well as prior to initiating a procedure in an operating room.

Additionally or alternatively to any GUI interface options or controls discussed, voice activated controls may be provided.

In addition to computing device aspects, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects stored herein.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout the description and claims of this specification, singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

The invention claimed is:

1. A computer implemented method comprising:
    accessing an image of a musculoskeletal structure of a patient and displaying the image via a display device;
    defining a reference axis of the musculoskeletal structure;
    rendering and overlaying a 3D implant in a first position over the image, the first position defined relative to the reference axis;
    receiving input to define a second position for the 3D implant, the second position defined relative to the reference axis;
    rendering and overlaying the 3D implant in association with the second position over the image;
    determining and storing a delta measurement comprising a difference between the first position and the second position; and
    providing the delta measurement for display via the display device.

2. The computer implemented method of claim 1 comprising receiving input to store the first position as a reference position for the 3D implant in a storage device.

3. The computer implemented method of claim 2 comprising rendering and overlaying a further graphical element representing the 3D implant in the reference position to distinguish the 3D implant as overlaid in the second position.

4. The computer implemented method of claim 1 wherein the 3D implant is overlaid in alignment with a corresponding implant structure of the patient in the image and wherein the first position provides a measurement of the corresponding implant structure relative to the reference axis.

5. The computer implemented method of claim 1 comprising displaying, via the display device, a current position of the 3D implant relative to the reference axis.

6. The computer implemented method of claim 5 comprising updating the displaying of the current position in response to a movement of the 3D implant.

7. The computer implemented method of claim 1 comprising providing a graphical user interface (GUI) to display handles for the 3D implant and to receive input to move the 3D implant over the image using the handles.

8. The computer implemented method of claim 1 comprising receiving input to define the first position via the handles for the 3D implant.

9. The computer implemented method of claim 8 wherein the input defines a fit for the 3D implant over an implant in the patient visible in the image.

10. The computer implemented method of claim 1 comprising fitting the 3D implant over an implant in the patient visible in the image using image processing.

11. The computer implemented method of claim 1 comprising providing a GUI to receive measurement data relative to the reference axis and rendering and overlaying the 3D implant in accordance with the measurement data.

12. The computer implemented method of claim 1 wherein the musculoskeletal structure comprises a hip structure and the 3D implant comprises a cup implant.

13. The computer implemented method of claim 1 wherein the first position and the second position are defined in accordance with an inclination angle and an anteversion angle.

14. The computer implemented method of claim 1 wherein the method is performed preoperatively using a computer apparatus configured to provide a preoperative planning system and wherein the method comprises communicating the delta measurement to a computing apparatus configured to provide an intraoperative surgical system to facilitate a surgical procedure.

15. The computer implemented method of claim 1 wherein the image comprises either:
    a preoperative image displayed preoperatively; or
    an intraoperative image displayed intraoperatively.

16. The computer implemented method of claim 1 comprising determining the delta measurement as angles of change relative to an existing implant in the patient as represented by the 3D implant in the first position and the 3D implant in the second position.

17. The computer implemented method of claim 1 wherein the delta measurement is communicated for further processing.

18. The computer implemented method of claim 17 wherein the further processing is surgical navigation on the patient in the image using an intra-operative surgical navigation system, and the first position is the same as a measured implant position for an implant in the patient as measured by the intra-operative surgical navigation system and wherein the intra-operative surgical navigation system is configured to measure a change to an implant position relative to the measured implant position.

19. The computer implemented method of claim 1 wherein the image defines a first image and the method comprises:
    accessing a second image of the musculoskeletal structure of the patient and displaying the second image via the display device together with the first image;

determining a spatial transformation between the first image and the second image;

rendering and overlaying the 3D implant in the first position over the second image based on the reference axis and the spatial transformation to display the 3D implant respectively on both of the first image and the second image; and, in response to receiving input to define the second position, rendering and overlaying the 3D implant in association with the second position over the second image.

20. The computer implemented method of claim 19 comprising providing handles to interact with the 3D implant as overlaid on each of the first image and the second image and wherein the input to define the second position for the 3D implant comprises receiving input via the handles as provided on one of the first image and the second image.

21. The computer implemented method of claim 19 wherein the first image and the second image comprise different views of the same functional position.

22. A computer system comprising at least one processing unit and a memory coupled to the at least one processing unit, the storage device storing instructions, which when executed by the at least one processing unit configure the computer system to:

access an image of a musculoskeletal structure of a patient and displaying the image via a display device;

define a reference axis of the musculoskeletal structure;

render and overlay a 3D implant in a first position over the image, the first position defined relative to the reference axis;

receive input to define a second position for the 3D implant, the second position defined relative to the reference axis;

render and overlay the 3D implant in association with the second position over the image;

determine and store a delta measurement comprising a difference between the first position and the second position; and provide the delta measurement for display via the display device.

* * * * *